US010202567B2

(12) United States Patent
Stolaroff et al.

(10) Patent No.: US 10,202,567 B2
(45) Date of Patent: Feb. 12, 2019

(54) BIOREACTORS INCLUDING ENZYME-EMBEDDED MULTICOMPONENT POLYMERS

(71) Applicant: Lawrence Livermore National Security, LLC, Livermore, CA (US)

(72) Inventors: Joshuah K. Stolaroff, Oakland, CA (US); Roger Aines, Livermore, CA (US); Sarah Baker, Dublin, CA (US); Craig D. Blanchette, Concord, CA (US); Amitesh Maiti, San Ramon, CA (US); John Vericella, Oakland, CA (US); James S. Oakdale, Castro Valley, CA (US)

(73) Assignee: LAWRENCE LIVERMORE NATIONAL SECURITY, LLC, Livermore, CA (US)

( * ) Notice: Subject to any disclaimer, the term of this patent is extended or adjusted under 35 U.S.C. 154(b) by 3 days.

(21) Appl. No.: 15/003,257

(22) Filed: Jan. 21, 2016

(65) Prior Publication Data
US 2017/0211026 A1    Jul. 27, 2017

(51) Int. Cl.
| | |
|---|---|
| C12M 1/40 | (2006.01) |
| C12N 11/04 | (2006.01) |
| C12N 11/08 | (2006.01) |
| C12M 1/04 | (2006.01) |
| C12M 1/00 | (2006.01) |
| B29C 64/00 | (2017.01) |
| B33Y 10/00 | (2015.01) |
| B33Y 80/00 | (2015.01) |

(52) U.S. Cl.
CPC ............. *C12M 21/18* (2013.01); *B29C 64/00* (2017.08); *C12M 23/24* (2013.01); *C12M 45/04* (2013.01); *C12N 11/04* (2013.01); *C12N 11/08* (2013.01); *B33Y 10/00* (2014.12); *B33Y 80/00* (2014.12)

(58) Field of Classification Search
CPC ...... C12M 21/18; C12M 23/24; C12M 45/04; C12M 25/02; C12M 25/10; C12N 11/04; C12N 11/08; C12N 11/00; C12N 11/02; C12N 11/14; B33Y 80/00; B33Y 10/00; B29C 64/00
See application file for complete search history.

(56) References Cited

U.S. PATENT DOCUMENTS

| | | | | |
|---|---|---|---|---|
| 4,266,026 A | * | 5/1981 | Breslau | ................ B01D 69/08 |
| | | | | 210/632 |
| 4,978,619 A | * | 12/1990 | Kajiwara | ............... C12N 11/04 |
| | | | | 435/180 |
| 5,116,506 A | * | 5/1992 | Williamson | ............ B01D 53/22 |
| | | | | 210/150 |
| 6,051,389 A | * | 4/2000 | Ahl | ......................... C12N 11/02 |
| | | | | 435/10 |
| 6,576,449 B2 | | 6/2003 | Clark et al. | |
| 2006/0090644 A1 | | 5/2006 | Sirkar | |
| 2011/0244029 A1 | * | 10/2011 | Barenholz | ............... A61K 9/127 |
| | | | | 424/450 |
| 2013/0267004 A1 | | 10/2013 | Rambo et al. | |

FOREIGN PATENT DOCUMENTS

| | | | | |
|---|---|---|---|---|
| EP | 0160266 A2 | * | 11/1985 | ............. A61K 9/127 |
| JP | 2001275653 A | * | 10/2001 | |

OTHER PUBLICATIONS

JP 2001-275653A. Oct. 9, 2001. Derwent Abstract. (Year: 2001).*
International Search Report and Written Opinion from PCT Application No. PCT/US2017/014444, dated Apr. 4, 2017.
Varicella et al. "Encapsulated liquid sorbents for carbon dioxide capture," Nature Communications, Feb. 5, 2015, vol. 6, No. 7124, pp. 1-7.
Blanchette et al. "Printable enzyme-embedded materials for methane to methanol conversion," Nature Communications, Jun. 15, 2016, vol. 7, No. 11900, pp. 1-9.
Baker et al., U.S. Appl. No. 15/411,337, filed Jan. 20, 2017.
Stadtman et al., "Free radical-mediated oxidation of free amino acids and amino acid residues in proteins," Amino Acids, vol. 25, 2003, pp. 207-218.
Schmid et al., "Industrial Biocatalysis Today and Tomorrow," Nature, vol. 409, Jan. 11, 2001, pp. 258-268.
Bornscheuer et al., "Engineering the third wave of biocatalysis," Nature, vol. 485, May 10, 2012, pp. 185-194.
Agapakis et al., "Natural strategies for the spatial optimization of metabolism in synthetic biology," Nature Chemical Biology, vol. 8, May 2012, pp. 527-535.

(Continued)

*Primary Examiner* — Renee Claytor
*Assistant Examiner* — Susan E. Fernandez
(74) *Attorney, Agent, or Firm* — Zilka-Kotab, P.C.

(57) ABSTRACT

According to one general embodiment, a membrane, includes a polymeric network configured to separate a first fluid and a second fluid, where the first and second fluids are different; and a plurality of enzymatic reactive components embedded within the polymeric network. According to another embodiment, a bioreactor includes a lattice of three dimensional structures, each structure including a membrane having: a polymeric network configured to separate a first fluid and a second fluid, where the first and second fluids are different; and a plurality of enzymatic reactive components embedded within the polymeric network.

18 Claims, 14 Drawing Sheets

(56) References Cited

OTHER PUBLICATIONS

Stolaroff et al., "A review of methane mitigation technologies with application to rapid release of methane from the Arctic," Environmental Science and Technology, vol. 46, No. 12, 2012, pp. 6455-6469.
Wrede et al., "Aerobic and anaerobic methane oxidation in terrestrial mud volcanoes in the Northern Apennines," Sedimentary Geology, Jul. 1, 2012, pp. 210-219.
Balasubramanian et al., "Oxidation of methane by a biological dicopper centre," Nature, vol. 465, May 6, 2010, pp. 115-119.
Miller et al., "The Solubility of Hydrocarbon Gases in Lipid Bilayers," Chemistry and Physics of Lipids, vol. 20, No. 3, Nov. 1977, pp. 229-241.
Chen et al., "Designing biological compartmentalization," Trends in Cell Biology, vol. 22, No. 12, Dec. 2012, pp. 662-670.
Nieguth et al., "Enabling Industrial Biocatalytic Processes by Application of Silicone-Coated Enzyme Preparations," Advanced Synthesis & Catalysis, vol. 353, No. 13, Sep. 2011, pp. 2522-2528.
Garcia-Galan et al., "Potential of Different Enzyme Immobilization Strategies to Improve Enzyme Performance," Advanced Synthesis & Catalysis, vol. 353, No. 16, Nov. 2011, pp. 2885-2904.
Tran et al., "Perspective of Recent Progress in Immobilization of Enzymes," ACS Catalysis, Jul. 2011, pp. 956-968.
Sheldon, R., "Enzyme Immobilization: The Quest for Optimum Performance," Advanced Synthesis &; Catalysis, vol. 349, Jun. 4, 2007, pp. 1289-1307.
Kim et al., "New materials for methane capture from dilute and medium-concentration sources," Nature Communications, vol. 4, 2013, p. 1694.
Baker et al., "Hydrogen Production by a Hyperthermophilic Membrane-Bound Hydrogenase in Soluble Nanolipoprotein Particles," Journal of the American Chemical Society, Nov. 18, 2008, 15 pages.
Baker et al., "Blood Clot Initiation by Mesocellular Foams: Dependence on Nanopore Size and Enzyme Immobilization," Langmuir, vol. 24, 2008, pp. 14254-14260.
Blanchette et al., "Characterization and Purification of Polydisperse Reconstituted Lipoproteins and Nanolipoprotein Particles," International Journal of Molecular Sciences, vol. 10, No. 7, Jul. 2009, pp. 2958-2971.
Gao et al., "Surface Functionalization of Gold Nanoparticles with Red Blood Cell Membranes," Advanced Materials, vol. 25, No. 26, Jul. 12, 2013, pp. 3549-3553.
Li et al., "Synthesis and Characterization of Amphiphilic Lipopolymers for Micellar Drug Delivery," Biomacromolecules, vol. 11, 2010, 2610-2620.
Kumar et al., "High-Density Reconstitution of Functional Water Channels into Vesicular and Planar Block Copolymer Membranes," Journal of the American Chemical Society, vol. 134, 2012, pp. 18631-18637.
Ansorge-Schumacher et al., "Directed evolution of formate dehydrogenase from Candida boidinii for improved stability during entrapment in polyacrylamide," FEBS Journal, vol. 273, 2006, pp. 3938-3945.
Avramescu et al., "Particle-loaded hollow-fiber membrane adsorbers for lysozyme separation," Journal of Membrane Science, vol. 322, 2008, pp. 306-313.
Koziol et al., "Toward a Small Molecule, Biomimetic Carbonic Anhydrase Model: Theoretical and Experimental Investigations of a Panel of Zinc(II)Aza-Macrocyclic Catalysts," Journal of Inorganic Chemistry, vol. 51, 2012, pp. 6803-6812.
Baker et al., "Controlling Bioprocesses with Inorganic Surfaces: Layered Clay Hemostatic Agents," Chemistry of Materials, vol. 19, Aug. 2007, pp. 4390-4392.
Baker et al., "Functionalized Vertically Aligned Carbon Nanofibers as Scaffolds for Immobilization and Electrochemical Detection of Redox Active Proteins," Chemistry of Materials, vol. 18, 2006, pp. 4415-4422.

Yoon et al., "Nanofiber Near-Field Light-Matter Interactions for Enhanced Detection of Molecular Level Displacements and Dynamics," Nano Letters, vol. 13, No. 4, Mar. 2013, pp. 1440-1445.
Baker et al., "Covalent Functionalization for Biomolecular Recognition on Vertically Aligned Carbon Nanofibers," Chemistry of Materials, vol. 17, No. 20, Sep. 2005, pp. 4971-4978.
Lee et al., "Electrically Addressable Biomolecular Functionalization of Carbon Nanotube and Carbon Nanotiber Electrodes," Nano Letters, vol. 4, No. 9, Aug. 2004, pp. 1713-1716.
Baker et al., "Covalently Bonded Adducts of Deoxyribonucleic Acid (DNA) Oligonucleotides with Single-Wall Carbon Nanotubes: Synthesis and Hybridization," Nano Letters, vol. 2, No. 12, 2002, pp. 1413-1417.
Stolaroff, J. K., "Chapter 2: Requirements Framework," A Greenhouse-Gas Information System: Monitoring and Validating Emissions Reporting and Mitigation, Lawrence Livermore, Sandia, and Los Alamos National Laboratories and the NASA Jet Propulsion Laboratory, May 24, 2011, 28 pages.
Stolaroff, J. K., "Products and packaging and U.S. GHG Emissions," Product Policy Institute, Aug. 2009, pp. 1-10.
Stolaroff et al., "Design Issues in a Mandatory Greenhouse Gas Emissions Registry for the United States," Energy Policy, Jun. 2009, pp. 3463-3466.
Stolaroff et al., "Carbon Dioxide Capture from Atmospheric Air Using Sodium Hydroxide Spray," Environmental Science and Technology, vol. 42, No. 8, 2008, pp. 2728-2735.
He et al., "Controlling the diameter, monodispersity and solubility of apoA1 nanolipoprotein particles using telodendrimer chemistry," Protein Science, Aug. 2013, 10 pages, retrieved from http://www.ncbi.nlm.nih.gov/pmc/articles/PMC3832044/.
Chahine et al., "Effect of age and cytoskeletal elements on the indentation-dependent mechanical properties of chondrocytes," PLoS One, vol. 8, No. 4, Apr. 2013, pp. 1-12.
Fischer et al., "Colocalized delivery of adjuvant and antigen using nanolipoprotein particles enhances the immune response to recombinant antigens," Journal of American Chemical Society, Communication, Jan. 2013, 2044-2047.
Blanchette et al., "Enhanced Cellulose Degradation Using Cellulase-Nanosphere Complexes," PLoS One, vol. 7, No. 8, Aug. 1, 2012, pp. 1-7.
Gao et al., "Characterizing diffusion dynamics of a membrane protein associated with nanolipoproteins using fluorescence correlation spectroscopy," Protein Science, 2011, pp. 437-447.
Blanchette et al., "Kinetic analysis of His-tagged protein binding to nickel-chelating nanolipoprotein particles," Bioconjugate Chemistry, Jul. 2010, pp. 1321-1330.
Fischer et al., "Conjugation to nickel-chelating nanolipoprotein particles increases the potency and efficacy of subunit vaccines to prevent West Nile encephalitis," Bioconjugate Chemistry, vol. 21, May 2010, pp. 1018-1022.
=Fischer et al., "Isolation, characterization, and stability of discretely-sized nanolipoprotein particles assembled with apolipophorin-III," PLoS One, Jul. 19, 2010, pp. 1-10.
Longo et al., "Imaging Cerebroside-rich Domains for Phase and Shape Characterization in Binary and Ternary Mixtures," Biochemica et Biophysics Acta—; Biomembranes, 2010, pp. 1357-1367.
Blanchette et al., "Decoupling Internalization, Acidification and Phagosomal-Endosomal/lysosomal Fusion during Phagocytosis of Internalin A Coated Beads in Epithelial Cells," PLoS One, Dec. 24, 2008, pp. 1-43.
Hansen et al., "High-Throughput Printing via Microvascular Multinozzle Arrays," Advanced Materials, vol. 25, Jan. 4, 2013, pp. 96-102.
Hopkins et al., "Modeling and Generating Parallel Flexure Elements," Precision Engineering, vol. 38, No. 3, Jul. 2014, pp. 525-537.
Maiti et al., "Atomistic modeling of CO2 capture in primary and tertiary amines—heat of absorption and density changes," Chemical Physics Letters, vol. 509, Jun. 2011, pp. 25-28.
Maiti, A, "Theoretical screening of Ionic Liquid solvents for carbon capture," Chemistry and Sustainability, Apr. 22, 2009, pp. 1-3.
Maiti et al., "Solvent screening for a hard-to-dissolve molecular crystal," Physical Chemistry Chemical Physics, vol. 10, 2008, pp. 5050-5056.

(56) References Cited

OTHER PUBLICATIONS

Han et al., "Solubility and recrystallization of 1,3,5-Triamino-2,4,6-trinitrobenzene in 3-ethyl-1-methylimidazolium acetate-DMSO co-solvent system," New Journal of Chemistry, vol. 33, No. 1, 2009, pp. 50-56.
Wescott et al., "Conductivity of carbon nanotube polymer composites," Applied Physics Letters, Nov. 27, 2006, pp. 1-13.
EIA, "Annual Energy Outlook 2015," US Energy Information Administration, Apr. 2015, 154 pages.
Bruns et al., "Amphiphilic Network as Nanoreactor for Enzymes in Organic Solvents," Nano Letters, vol. 5, No. 1, 2005, pp. 45-48.
Alexander et al., "Summary for Policymakers," Climate Change 2013: The Physical Science Basis, Contribution of Working Group I to the Fifth Assessment Report of the Intergovernmental Panel on Climate Change, 2013, pp. 3-29.
Nguyen et al., "The Particulate Methane Monooxygenase from *Methylococcus capsulatus* (Bath) Is a Novel Copper-containing Three-subunit Enzyme," Journal of Biological Chemistry, vol. 273, No. 14, Apr. 1998, pp. 7957-7966.
Rios et al., "Progress in enzymatic membrane reactors—a review," Journal of Membrane Science, vol. 242, 2004, pp. 189-196.
Culpepper et al., "Evidence for Oxygen Binding at the Active Site of Particulate Methane Monooxygenase," Journal of the American Chemical Society, vol. 134, No. 18, May 2012, pp. 7640-7643.
Flickinger et al., "Painting and Printing Living Bacteria: Engineering Nanoporous Biocatalytic Coatings to Preserve Microbial Viability and Intensify Reactivity," Biotechnology Progress, vol. 23, 2007, pp. 2-17.
Choi et al., "The Membrane-Associated Methane Monooxygenase (pMMO) and pMMO-NADH:Quinone Oxidoreductase Complex from *Methylococcus capsulatus* Bath," Journal of Bacteriology, Oct. 2003, pp. 5755-5764.
Sirajuddin et al., "Effects of Zinc on Particulate Methane Monooxygenase Activity and Structure," Journal of Biological Chemistry, 2014, pp. 1-31.
Phelps et al., "Maleimide cross-linked bioactive PEG hydrogel exhibits improved reaction kinetics and cross-linking for cell encapsulation and in-situ delivery," Advanced Materials, Jan. 2013, pp. 1-12.
Park et al., "Preparation of Water-Swollen Hydrogel Membranes for Gas Separation," Journal of Applied Polymer Science, vol. 80, 2001, pp. 1785-1791.
Whittenbury et al., "Enrichment, Isolation and Some Properties of Methane-utilizing Bacteria," Journal of General Microbiology, vol. 61, 1970, pp. 205-218.
Zheng et al., "Ultra-light, Ultra-stiff Mechanical Metamaterials," Science, vol. 344, May 2014, 28 pages.
Yagci et al., "Photoinitiated Polymerization: Advances, Challenges, and Opportunities," Macromolecules Perspective, vol. 43, 2010, pp. 6245-6260.
Maiti et al., "SnO2 nanoribbons as NO2 sensors: insights from First-Principles calculations," Nano Letters, vol. 3, No. 3, May 2003, pp. 1025-1028.
Maiti et al., "Effect of adsorbates on field-emission from carbon nanotubes," Physical Review Letters, vol. 87, No. 15, Oct. 2001, p. 155502.
Tobis et al., "Amphiphilic polymer conetworks as chiral separation membranes," Journal of Membrane Science, vol. 372, Apr. 15, 2011, pp. 219-227.
Lee et al., "Fabrication of Nanofiber Microarchitectures Localized within Hydrogel Microparticles and Their Application to Protein Delivery and Cell Encapsulation," Advanced Functional Materials, vol. 23, No. 5, Feb. 5, 2013, pp. 591-597.
Arakawa et al., "Catalysis Research of Relevance to Carbon Management: Progress, Challenges, and Opportunities," Chem. Rev., vol. 101, 2001, pp. 953-996.
Haynes et al., "Rethinking biological activation of methane and conversion to liquid fuels," Nature Chemical Biology, vol. 10, 2014, pp. 331-339.
Hammond et al., "Direct Catalytic Conversion of Methane to Methanol in an Aqueous Medium by using Copper-Promoted Fe-ZSM-5," Angewandte Chemie International Edition, vol. 51, No. 21, Apr. 2012, pp. 5129-5133.
Conrado et al., "Envisioning the Bioconversion of Methane to Liquid Fuels," Science, vol. 343, 2014, pp. 621-623.
Sirajuddin et al., "Enzymatic Oxidation of Methane," Biochemistry, vol. 54, No. 14, 2015, pp. 2283-2294.
Lin et al., "Gas Permeation and Diffusion in Cross-Linked Poly(ethylene glycol diacrylate)," Macromolecules, vol. 39, 2006, pp. 3568-3580.
Lin et al., "Gas and Vapor Solubility in Cross-Linked Poly(ethylene Glycol Diacrylate)," Macromolecules, vol. 38, 2005, pp. 8394-8407.
Chen et al., "Bacteriohemerythrin bolsters the activity of the particulate methane monooxygenase (pMMO) in Methylococcus capsulatus," Journal of Inorganic Biochemistry, vol. 111, Jun. 2012, pp. 10-17.
Lin et al., "The Effect of Cross-Linking on Gas Permeability in Cross-Linked Poly(Ethylene Glycol Diacrylate)," Macromolecules, vol. 38, Sep. 10, 2005, pp. 8381-8393.
Liu et al., "Gas permeation through water-swollen hydrogel membranes," Journal of Membrane Science, vol. 310, Mar. 2008, pp. 66-75.
Padmavathi et al., "Structural Characteristics and Swelling Behavior of Poly(ethylene glycol) Diacrylate Hydrogels," Macromolecules, vol. 29, 1996, pp. 1976-1979.
Mellott et al., "Release of protein from highly cross-linked hydrogels of poly(ethylene glycol) diacrylate fabricated by UV polymerization," Biomaterials, vol. 22, 2001, pp. 929-941.
Cruise et al., "Characterization of permeability and network structure of interfacially photopolymerized poly(ethylene glycol) diacrylate hydrogels," Biomaterials, vol. 19, Jul. 1998, pp. 1287-1294.
Garrison, W. M., "Reaction mechanisms in the radiolysis of peptides, polypeptides, and proteins," Chemical Reviews, vol. 87, 1987, pp. 381-398.
Raharjo et al., "Pure and mixed gas CH4 and n-C4H10 permeability and diffusivity in poly(dimethylsiloxane)," Journal of Membrane Science, vol. 306, 2007, pp. 75-92.
Petri et al., "Efficient immobilization of epoxide hydrolase onto silica gel and use in the enantioselective hydrolysis of racemic para-nitrostyrene oxide," Journal of Molecular Catalysis B: Enzymatic, vol. 32, 2005, pp. 219-224.
Moelans et al., "Immobilisation behaviour of biomolecules in mesoporous silica materials," Catalysis Communications, vol. 6, 2005, pp. 591-595.
Borole et al., "Performance of chloroperoxidase stabilization in mesoporous sol-gel glass using in situ glucose Oxidase peroxide generation," Applied Biochemistry and Biotechnology, vol. 113, No. 1, Mar. 2004, pp. 273-285.
Wang et al., "Biocatalytic plastics as active and stable materials for biotransformations," Nature Biotechnology, vol. 15, 1997, pp. 789-793.
Kim et al., "Complete Oxidation of Methanol in Biobattery Devices Using a Hydrogel Created from Three Modified Dehydrogenases," Angewandte Chemie International Edition, vol. 52, 2013, pp. 1437-1440.
Fedorovich et al., "Hydrogels as Extracellular Matrices for Skeletal Tissue Engineering: State-of-the-Art and Novel Application in Organ Printing," Tissue Engineering, vol. 13, 2007, pp. 1905-1925.
Mironov et al., "Organ printing: computer-aided jet-based 3D tissue engineering," Trends in Biotechnology, vol. 21, 2003, pp. 157-161.
Zhang, Y. H., "Substrate channeling and enzyme complexes for biotechnological applications," Biotechnology Advances, vol. 29, 2011, pp. 715-725.
Majima et al., "Phenyl-2,4,6-trimethylbenzoylphosphinates as water-soluble photoinitiators. Generation and reactivity pf O=P(C6H5)(O-) radical anions," Macromolecular Chemistry and Physics, vol. 192, 1991, pp. 2307-2315.
Duoss et al., "Three-Dimensional Printing of Elastomeric, Cellular Architectures with Negative Stiffness," Advanced Functional Materials, vol. 24, 2014, pp. 4905-4913.

(56) References Cited

OTHER PUBLICATIONS

Baker et al., "Detection of bio-organism simulants using random binding on a defect-free photonic crystal," Applied Physics Letters, vol. 97, 2010, pp. 113701-113701-3.

Goldman et al., "Synthesis of glycine-containing complexes in impacts of comets on early Earth," Nature Chemistry, vol. 2, Nov. 2010, pp. 949-954.

Green et al., "Perry's Chemical Engineers' Handbook," McGraw-Hill, 8th Edition, 2008, 2,735 pages.

Restriction Requirement from U.S. Appl. No. 15/411,337, dated Aug. 31, 2018.

* cited by examiner

US 10,202,567 B2

BIOREACTORS INCLUDING ENZYME-EMBEDDED MULTICOMPONENT POLYMERS

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The present invention relates to bioreactors, and more particularly to bioreactors that include enzyme-embedded multicomponent polymers.

BACKGROUND

Most chemical reactions of interest for clean energy are routinely carried out in nature. These reactions include the conversion of sunlight to chemical energy, the transfer of carbon dioxide into and out of solution, the selective oxidation of hydrocarbons (including methane to methanol), the formation of C—C bonds (including methane to ethylene), and the formation and dissolution of Si—O bonds (including enhanced mineral weathering). Conventional industrial approaches to catalyze these reactions are either inefficient or have yet to be developed.

Certain enzymes have been identified that carry out each of the aforementioned reactions. Unfortunately, industrial biocatalysis is primarily limited to the synthesis of low-volume, high-value products, such as pharmaceuticals, due to narrow operating parameters required to preserve biocatalyst activity. Enzyme catalyzed reactions are thus typically carried out in fermenters, which are closed, stirred, tank reactors configured to use bubbled gases for mass transfer. FIG. 1, illustrates a conventional stirred tank reactor 100, which may include a motor 102, an input/feed tube 104, a cooling jacket 106, one or more baffles 108, an agitator 110, one or more gas spargers 112, and an aqueous medium 114. Gas exchange in the stirred tank reactor 100 may be achieved by bubbling from the sparger(s) 112 at the bottom of the aqueous medium 114 and gas collection above said aqueous medium 114. Care must be taken to maintain a narrow set of conditions in such stirred tank reactors to favor the desired metabolic pathways and discourage competing pathways and competing organisms. Moreover, stirred tank reactors are energy inefficient, require batch processing, suffer from loss of catalytic activity due to enzyme inactivation, and exhibit slow rates of throughput due to low catalyst loading and limited mass-transfer.

To allow reuse of enzymes in stirred-tank reactors, and to improve stability in reactor conditions, enzymes may be immobilized on inert, artificial materials. As shown in FIG. 2, one conventional approach is to immobilize enzymes 202 on the surface of an inert material 204. Other conventional approaches may involve immobilizing enzymes on the surface of accessible pores of inert materials. However, such conventional enzyme immobilization techniques also suffer from lower volumetric catalyst densities, low throughput rates, and do not have routes for efficient gas delivery or product removal.

SUMMARY

According to one general embodiment, a membrane, includes a polymeric network configured to separate a first fluid and a second fluid, where the first and second fluids are different; and a plurality of enzymatic reactive components embedded within the polymeric network.

According to another embodiment, a bioreactor includes a lattice of three dimensional structures, each structure including a membrane having: a polymeric network configured to separate a first fluid and a second fluid, where the first and second fluids are different; and a plurality of enzymatic reactive components embedded within the polymeric network.

Other aspects and embodiments of the present invention will become apparent from the following detailed description, which, when taken in conjunction with the drawings, illustrate by way of example the principles of the invention.

BRIEF DESCRIPTION OF THE DRAWINGS

For a fuller understanding of the nature and advantages of the present invention, reference should be made to the following detailed description read in conjunction with the accompanying drawings.

DETAILED DESCRIPTION

Figure 1:
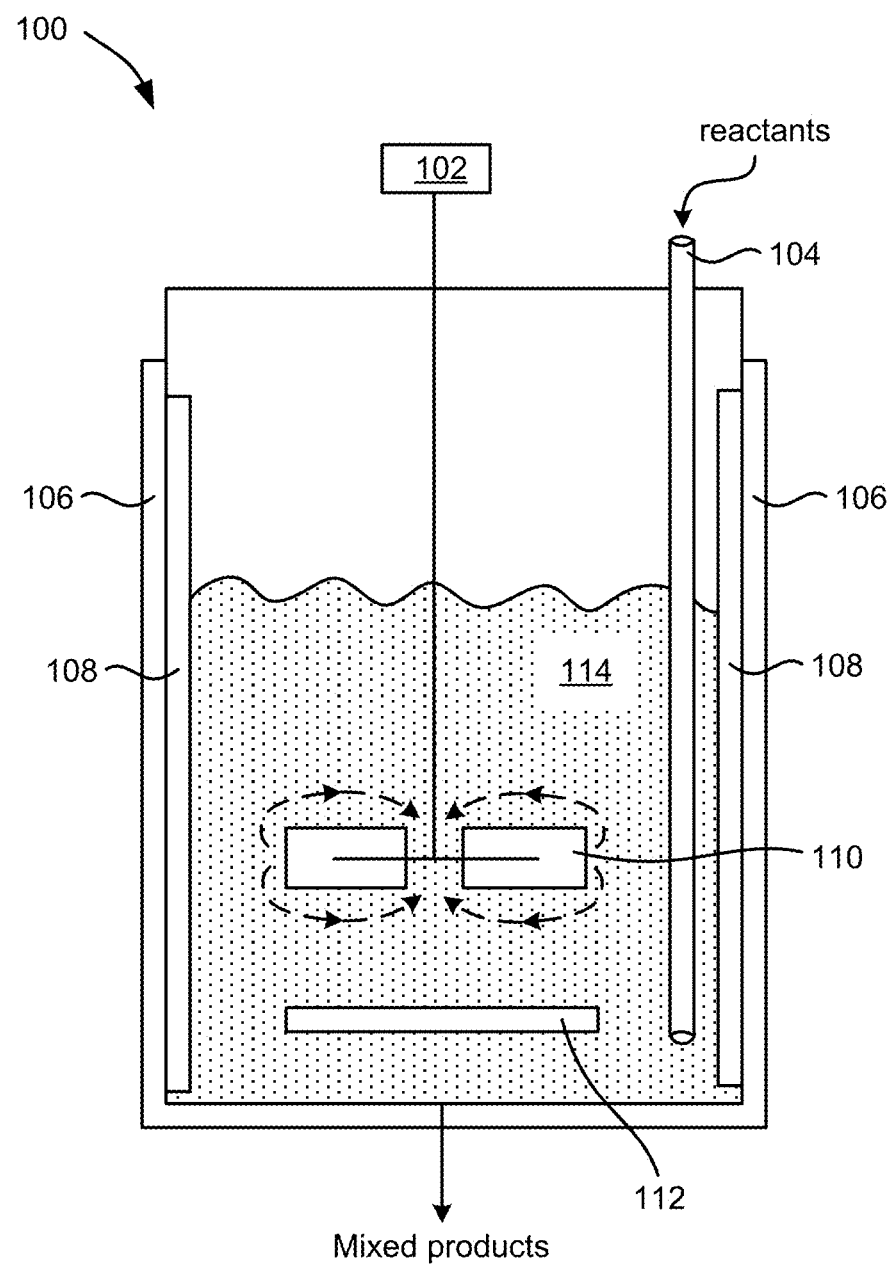
FIG. 1 is a schematic representation of a conventional stirred tank reactor, according to the prior art.
Figure 2:
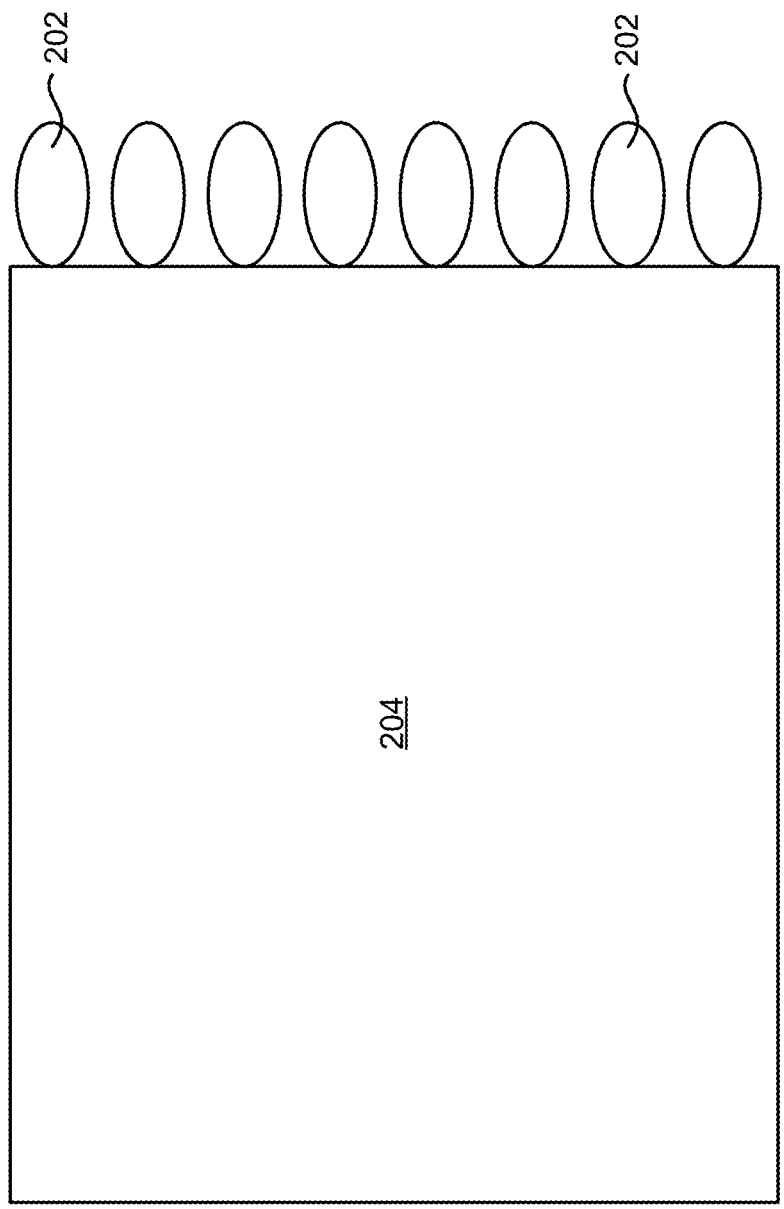
FIG. 2 is a schematic representation of enzymes immobilized on an exterior surface of an inert material, according to the prior art.

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

As also used herein, the term "about" when combined with a value refers to plus and minus 10% of the reference value. For example, a length of about 100 nm refers to a length of 100 nm±10 nm.

As further used herein, the term "fluid" may refer to a liquid or a gas.

As discussed previously, enzymes have been identified that catalyze virtually all of the reactions relevant to clean energy, such as selective transformations among carbon fuels, gas to liquids technology, storage of solar energy, exchange of $CO_2$, formation and dissolution of silicates, and neutralization of wastes. However, industrial enzyme biocatalysis is currently limited to low-volume, high-value products such as pharmaceuticals due to the narrow operating parameters required to preserve biocatalyst activity; slow rates of throughput due to low catalyst loading; limited mass transfer; and susceptibility to contamination and poisoning. These limitations require that many biocatalysis processes are carried out in single phase, aqueous media such as that provided in stirred tank reactors. However, stirred tank reactors are energy inefficient, require batch processing, and have poor mass transfer characteristics. While techniques have emerged to improve the stability and allow reuse of enzymes in stirred tank reactors, such techniques involve immobilizing the enzymes solely on the exterior surface(s) of an inert material or on the exterior surface(s) of the pores of an inert material. Unfortunately, these conventional immobilization techniques still fail to rectify the slow throughput rates and limited mass transfer associated with current biocatalysis processes.

To overcome the aforementioned drawbacks, embodiments disclosed herein are directed to a novel class of bioreactor that includes a membrane comprising one or more types of reactive enzymes and/or enzyme-containing cell fragments embedded within, and throughout the depth of, a multicomponent polymer network. In various approaches, this multicomponent polymer network may comprise two or more polymer types, or a mixture of a polymer and inorganic material. Preferably, the membrane comprises permeable, multi-component polymers that serve as both a mechanical support for the embedded enzymes, as well as functional materials configured to perform one or more additional functions of the bioreactor, such as: efficiently distributing reactants and removing products; exposing the embedded enzymes to high concentrations of reactants; separating reactants and products; forming high surface area structures for exposing the embedded enzymes to reactants; supplying electrons in hybrid enzyme-electrochemical reactions; consolidating enzymes with co-enzymes in nanoscale subdomains for chained reactions, etc. In additional approaches, this membrane may be molded into shapes/features/structures (e.g., hollow fibers, micro-capsules, hollow tube lattices, spiral wound sheets, etc.) to optimize the bioreactor geometry for mass transfer, product removal, and continuous processing.

The novel class of bioreactor disclosed herein may be especially suited to catalyze reactions that occur at phase boundaries, e.g., gas to liquid, liquid to gas, polar to non-polar, non-aqueous to aqueous, etc. Accordingly, the novel class of bioreactors disclosed herein may be useful for reactions in clean energy applications that involve a gas-phase reactant or product (e.g., methane to methanol conversion, $CO_2$ absorption, oxidation reactions with $O_2$, reduction reactions with $H_2$ or methane, $CO_2$ conversion to synthetic fuel, etc.), as well as reactions in the chemical and pharmaceutical industries that involve treatment of non-polar organic compounds with polar reactants (or vice versa).

The following description discloses several general, specific, and preferred embodiments relating to bioreactors based on enzyme-embedded multicomponent polymers arranged as nano-, micro- and/or millimeter-structures.

In one general embodiment, a membrane, includes a polymeric network configured to separate a first fluid and a second fluid, where the first and second fluids are different; and a plurality of enzymatic reactive components embedded within the polymeric network.

In another general embodiment, a bioreactor includes a lattice of three dimensional structures, each structure including a membrane having: a polymeric network configured to separate a first fluid and a second fluid, where the first and second fluids are different; and a plurality of enzymatic reactive components embedded within the polymeric network.

Figure 3:
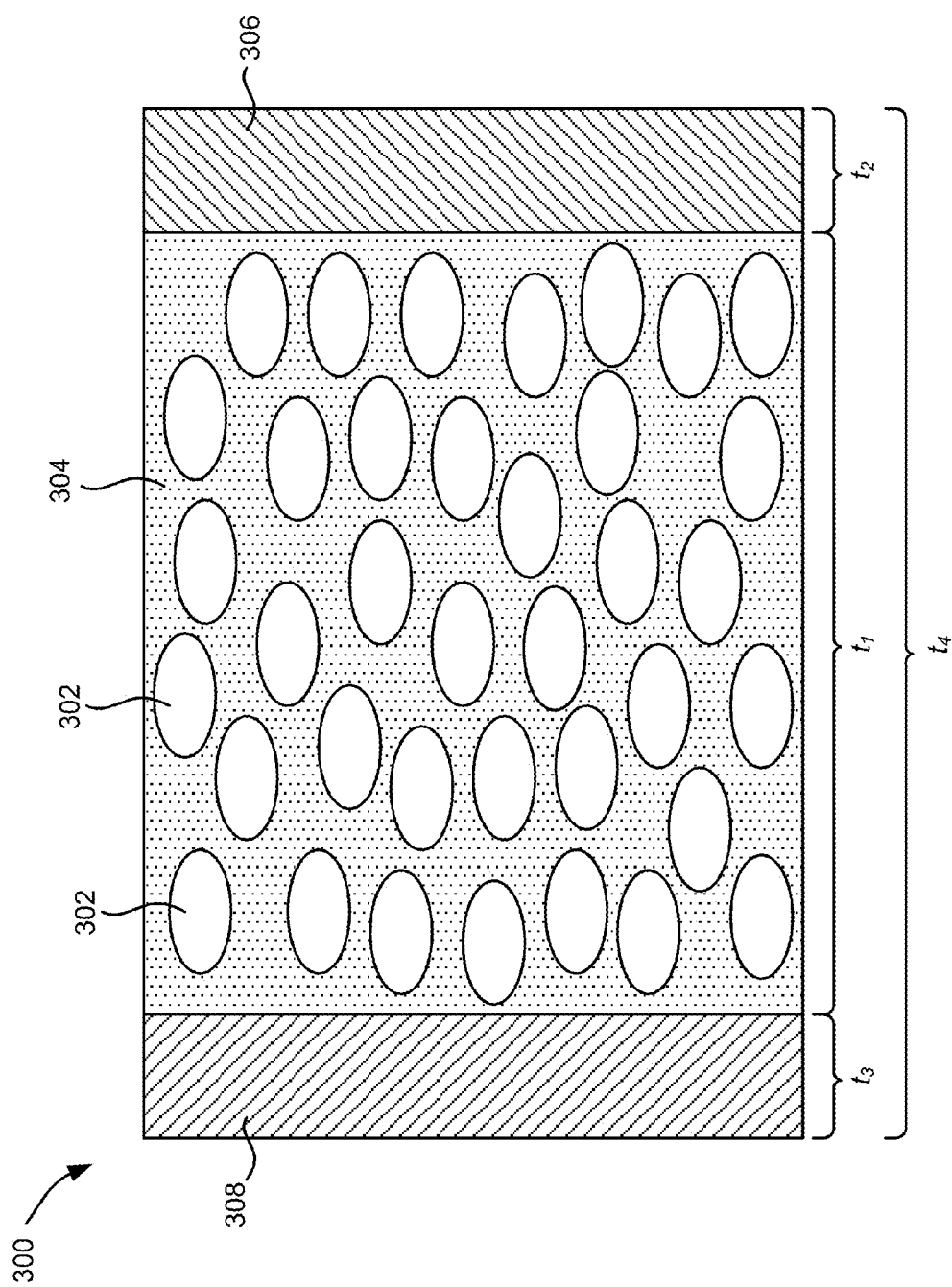
FIG. 3 is a schematic representation of enzymatic reactive components embedded within a polymeric network, according to one embodiment.

Referring now to FIG. 3, a membrane 300 particularly suitable for use in a bioreactor is shown according to one embodiment. As an option, the membrane 300 may be implemented in conjunction with features from any other embodiment listed herein, such as those described with reference to the other FIGS. Of course, the membrane 300 and others presented herein may be used in various applications and/or in permutations which may or may not be specifically described in the illustrative embodiments listed herein. For instance, the membrane 300 may be used in any desired environment and/or include more or less features, layers, etc. than those specifically described in FIG. 3.

As shown in FIG. 3, the membrane 300 includes a plurality of enzymatic reactive components 302 embedded within a polymer network 304. In various approaches, the enzymatic reactive components 302 may comprise about 1% to 80% of the mass of the polymer network 304. The enzymatic reactive components 302 may be configured to catalyze any of the reactions described herein, and in particular reactions that take place at phase boundaries (e.g., gas to liquid, liquid to gas, polar to non-polar, non-aqueous to aqueous, etc.).

In some approaches, the plurality of enzymatic reactive components 302 may comprise one or more of: isolated enzymes, trans-cell-membrane enzymes, cell-membrane-bound enzymes, liposomes coupled to/comprising an enzyme, etc. Stated another way, each enzymatic reactive component 302 may individually be selected from the group selected from: an isolated enzyme, a trans-cell-membrane enzyme, a cell-membrane-bound enzyme, and a liposome coupled to/comprising an enzyme. Suitable enzymatic reactive components 302 may include, but are not limited to, formate dehydrogenase, carbonic anhydrase, cytochrome p450, hydrogenase, particulate methane monooxygenasae (pMMO), photosynthetic complexes, etc. Moreover, while each of the enzymatic reactive components 302 may be the same (e.g., comprise the same structure and/or composition) in particular approaches; other approaches may require at least two of the enzymatic reactive components 302 to be different (e.g., have a different structure and/or composition) from one another.

In approaches where at least one of the enzymatic reactive components 302 includes a membrane-bound enzyme, said enzyme may be stabilized prior to incorporation into the polymer network 304. For instance, in one stabilization approach, cell fragments comprising the enzyme of interest may be used, and directly incorporated into the polymer network 304. In another stabilization approach, a lipopolymer may first be formed by linking a lipid to a polymer of interest. The lipid region of the polymer may spontaneously insert into the cell membrane, thereby creating a polymer functionalized liposome, which may be incorporated in the polymer network 304. In yet another stabilization approach, the enzyme of interest may be coupled to and/or encapsulated into a nano-lipo-protein particle (NLP), which may then be incorporated in the polymer network 304.

The enzymatic reactive components 302 may be incorporated into the polymeric network 304 via several methods including, but not limited to: attaching the enzymatic reactive components 302 to electrospun fibers of a first polymer, and backfilling with a second polymer (see, e.g., the method described in FIG. 4); directly incorporating the enzymatic reactive component 302 into a polymer or block-copolymer network before or after crosslinking the network (see, e.g., the method described in FIG. 5); and other suitable incorporation methods as would become apparent to one having skill in the art upon reading the present disclosure.

With continued reference to FIG. 3, the polymeric network 304 may include at least a two phase polymer network, e.g. a polymer network comprising two or more polymeric materials. This polymer network 304 may be configured to serve as a mechanical support for the enzymatic reactive components 302 embedded therein, concentrate reactants, and remove products. In preferred approaches, the polymeric network 304 may include nanometer scale domains of higher reactant permeability, as well as nanometer scale domains of higher product permeability.

In particular approaches involving gas to liquid reactions, the polymeric network may include nanometer scale domains of higher gas permeability, such as silicon, as well as nanometer scale domains of higher product permeability, such as a polyethylene glycol (PEG) based hydrogel. These domains of high gas permeability typically also have higher gas solubility, increasing the local concentration of reactants (e.g., relative to the aqueous medium in a stirred tank reactor) and therefore increase the turnover frequency of the enzymatic reactive components 302; whereas, the domains of low gas permeability and high product permeability may efficiently remove the product and reduce product inhibition (thereby also increasing the turnover frequency and stability of the enzymatic reactive components 302) or serve to stabilize the enzymatic reactive components. In various approaches, the permeability for the "higher gas permeability phase" may be greater than 100 barrer.

In some approaches, the polymer network 304 may comprises a di-block copolymer network. In other approaches, the polymer network 304 may include a tri-block copolymer network. Suitable polymers for the polymeric network 304 may include silicone polymers, polydimethylsiloxane (PDMS), poly(2-methyl-2-oxazoline) (PMOXA), polyimide, PEG, polyethylene glycol diacrylate (PEGDA), poly (lactic acid) (PLA), polyvinyl alcohol (PVA), and other such polymers compatible with membrane proteins and block copolymer synthesis as would become apparent to one skilled in the art upon reading the present disclosure. In more approaches, each polymer in the polymeric network 304 may have a molecular weight ranging from about 500 Daltons to about 500 kiloDaltons.

In other approaches, the polymeric network 304 may include a mixture of at least one polymer material and at least one inorganic material.

In various approaches, a thickness, $t_1$, of the enzyme embedded polymer network 304 may be in a range from about 1 micrometer to about 2 millimeters.

As indicated above, the membrane 300 may be configured to separate the reactants and products associated with a catalyzed reaction of interest. These reactants and products may be two different fluids, such as liquids and gasses, aqueous species and non-aqueous species, polar species and non-polar species, etc. In one exemplary approach where the membrane 300 may be configured to separate methane and oxygen from methanol, the methane reactant concentration may be in a range from about 1 to about 100 mM, the oxygen reactant concentration may be in a range from about 1 to about 100 mL, and the methanol product concentration range may be in a range from about 0.1 to about 1000 mM.

To further facilitate reactant-production separation, at least a portion of one surface of the membrane 300 may include an optional reactant permeable polymer layer 306 coupled thereto, as shown in FIG. 3. In preferred approaches, this reactant permeable polymer layer 306 may also be impermeable to products generated from the reactions catalyzed by the enzymatic reactive components 302. Suitable polymeric materials for this reactant permeable polymer layer 306 may include, but are not limited to, nanofiltration, reverse-osmosis, or chemically selective membranes, such as poly(ethylene imine), PVA, poly(ether ether ketone) (PEEK), cellulose acetate, or polypropylene (PP). In some approaches, a thickness, $t_2$, of the reactant permeable polymer layer 306 may be in a range from about 0.1 to about 50 micrometers. This optional reactant permeable polymer layer 306 may be particularly suited for approaches involving an organic polar reactant and an organic non-polar product (and vice versa).

As also shown in FIG. 3, at least a portion of one surface of the membrane 300 may include an optional product permeable polymer layer 308 coupled thereto. This product permeable polymer layer 308 may preferably be coupled to a surface of the membrane 300 opposite that on which the reactant permeable polymer layer 306 is coupled, thereby facilitating entry of reactants (e.g., gaseous reactants) on one side of the membrane 300, and removal of the reaction products (e.g., liquid reaction products) on the opposing side of the membrane 300. In more preferred approaches, this product permeable polymer layer 308 may also be impermeable to the reactants introduced into the enzyme embedded polymer network 304. Suitable polymeric materials for this product permeable polymer layer 308 may include, but are not limited to, nanofiltration, reverse-osmosis, or chemically selective membranes, such as poly(ethylene imine), PVA, poly(ether ether ketone) (PEEK), cellulose acetate, or polypropylene (PP). In some approaches, a thickness, $t_3$, of the product permeable polymer layer 308 may be in a range from about 0.1 to about 50 micrometers.

In some approaches, one or more of the enzymatic reactive components 302 may require a cofactor for function. Accordingly, cofactors may be supplied by co-localized enzymes in reactor domains of the polymer network 304 (not shown in FIG. 3), and/or be retained within a cofactor impermeable layer coupled to a portion of the membrane 300 (not shown in FIG. 3).

In various approaches, a total thickness, $t_4$, of the membrane 300 may be in a range from about 10 to about 3100 micrometers.

In yet more approaches, the membrane 300 may be shaped into features, structures, configurations, etc. that provide a desired surface area to support efficient transport of reactants to, and products from, the enzymatic reactive components 302. For instance, the membrane 300 may be shaped into at least one of: a hollow fiber membrane, a micro-capsule membrane, a hollow tube membrane, a spiral wound membrane, etc.

Figure 4:
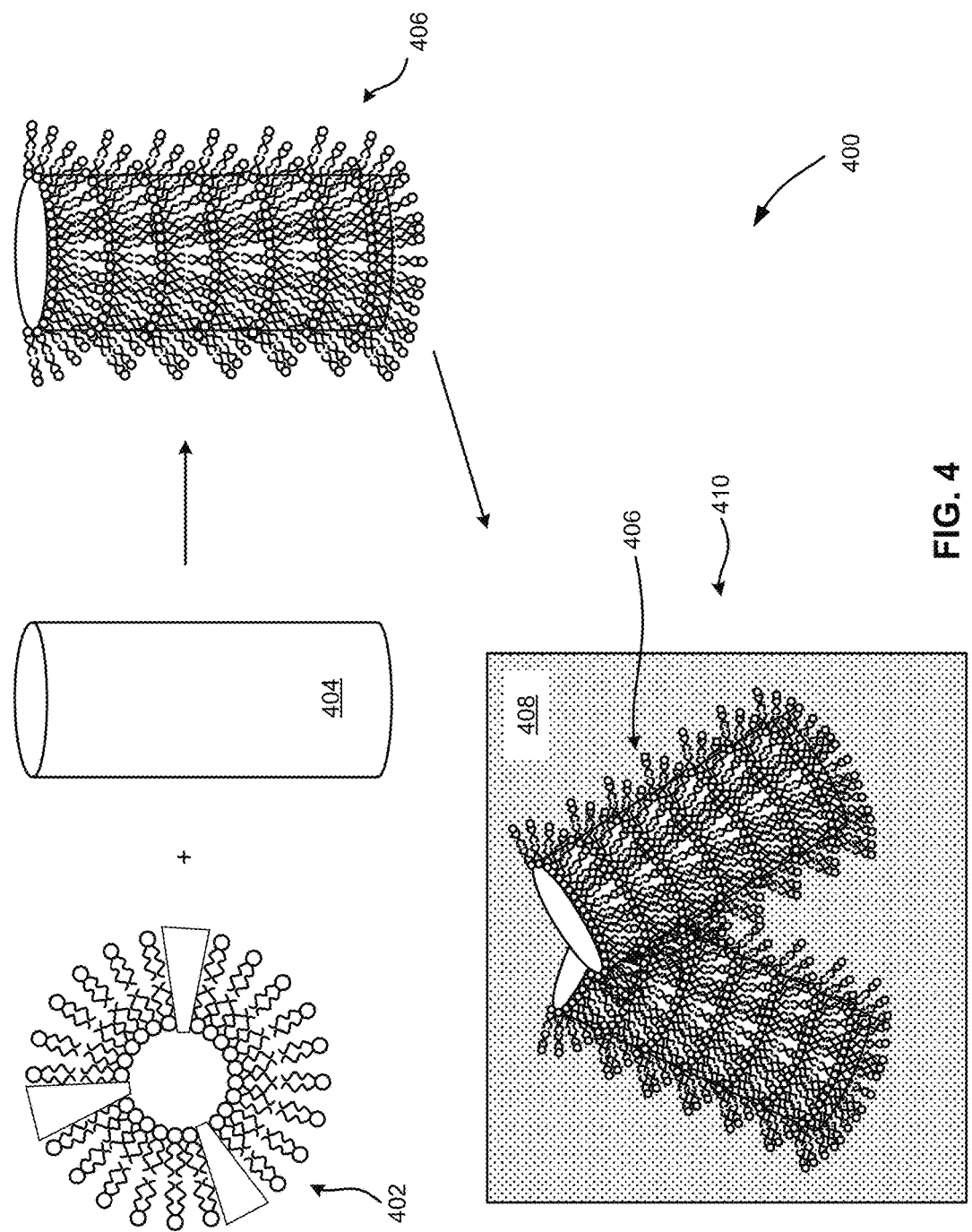
FIG. 4 is a process flow illustrating a method for embedding enzymatic reactive components within a two phase (AB) polymer network, according to one embodiment.

Referring now to FIG. 4, a method 400 for embedding enzymatic reactive components within a two phase (AB) polymer network is shown according to one embodiment. As an option, the present method 400 may be implemented in conjunction with features from any other embodiment listed herein, such as those described with reference to the other FIGS. Of course, this method 400 and others presented herein may be used to form structures for a wide variety of devices and/or purposes, which may or may not be related to the illustrative embodiments listed herein. It should be noted that the method 400 may include more or less steps than those described and/or illustrated in FIG. 4, according to various embodiments. It should also be noted that that the method 500 may be carried out in any desired environment.

As shown in FIG. 4, an enzymatic reactive component 402 is adsorbed to at least one portion of the exterior surface of polymer A 404, thereby forming enzyme-embedded polymer A 406. In preferred approaches, polymer A 404 may comprise one or more hydrophobic, reactant permeable (e.g., gas permeable) polymeric materials configured to provide high concentrations and fast transport of reactants. In further approaches, polymer A 404 may be a polymer nanofiber generated using electrospinning, extrusion, self-assembly, or other suitable technique as would become apparent to one skilled in the art upon reading the present disclosure. In additional approaches, such a polymer A nanofiber may be crosslinked to other polymer A nanofibers. In one exemplary approach, polymer A 404 comprises PDMS.

In various approaches, the enzymatic reactive component 402 may be selected from the group consisting of: an isolated enzyme, an enzyme comprising a cell fragment (e.g., a cell membrane or cell membrane fragment), and a liposome comprising/coupled to an enzyme. In some approaches, the enzymatic reactive component 402 may include at least one of: formate dehydrogenase, carbonic anhydrase, cytochrome p450, hydrogenase, particulate methane monooxygenasae (pMMO), photosynthetic complexes, etc.

In the non-limiting embodiment shown in FIG. 4, a plurality of enzymatic reactive components 402 may be adsorbed to one or more portions of the exterior surface of polymer A 404. These enzymatic reactive components 402 may be adsorbed to at least the majority, or more preferably about an entirety, of the exterior surface of polymer A 404. The lipid bilayer vesicles of the enzymatic reactive components 402 may spontaneously collapse on the exterior surface of polymer A 404, thereby forming a lipid-bilayer functionalized surface.

As further shown in FIG. 4, the enzyme-embedded polymer A 406 may be mixed with polymer B 408 to create the two phase (AB) polymer monolith 410 with the enzymatic reactive components 402 at the interface between the two phases. In preferred approaches, polymer B 408 may comprise one or more hydrophilic, product permeable polymeric materials configured to provide transport of products, as well as stabilize the enzymatic reactive components 402. For instance, in one specific approach, polymer B 408 may be a hydrophobic polymer hydrogel.

While the resulting polymeric network shown in FIG. 4 includes two phases (i.e., polymer A and polymer B), it is important to note that said polymeric network may include more than two phases in additional approaches.

Figure 5:
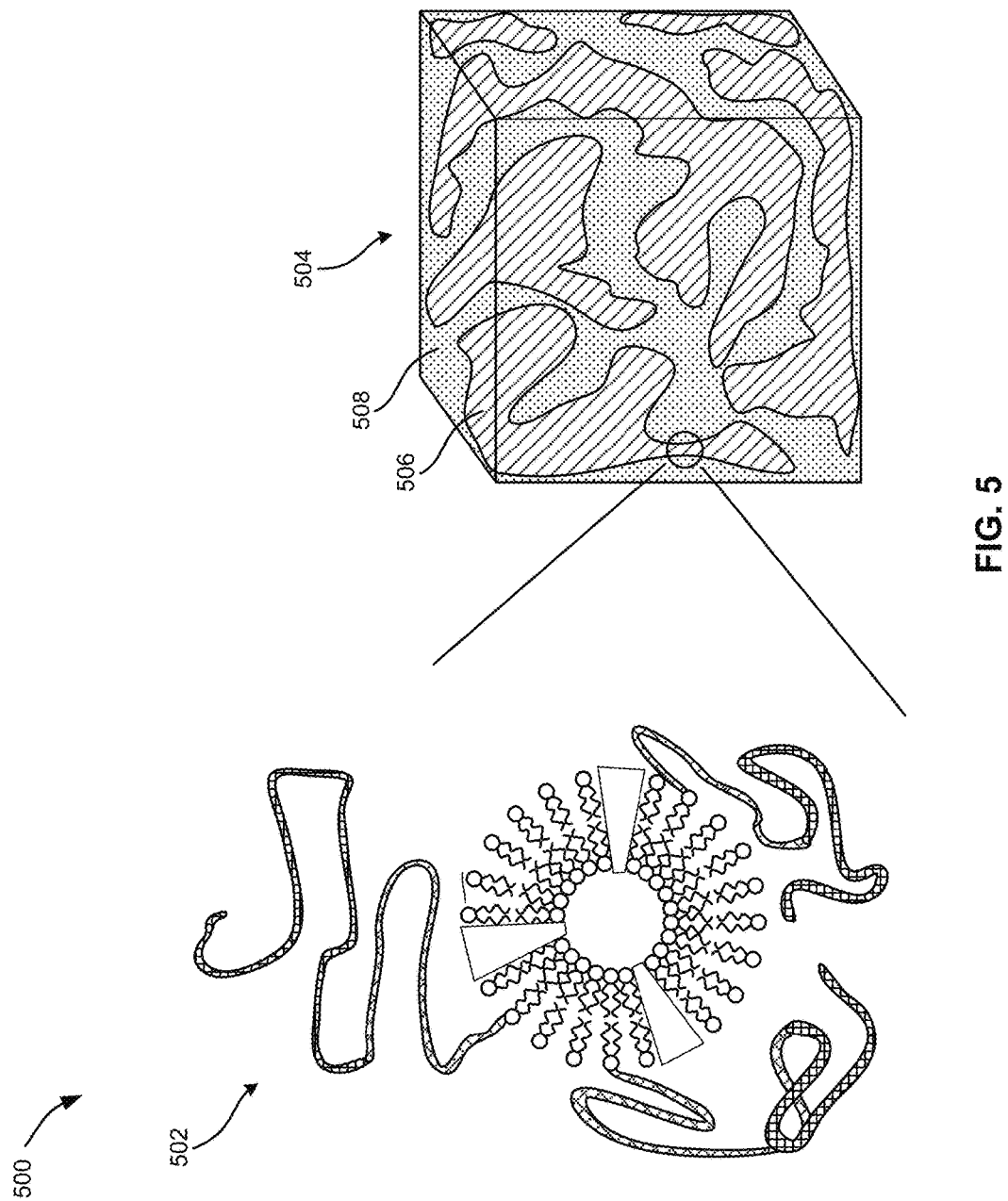
FIG. 5 is a process flow illustrating a method for embedding enzymatic reactive components within a two phase (AB) polymer network, according to another embodiment.

Referring now to FIG. 5, a method 500 for embedding enzyme reactive components within a two phase (AB) polymer network is shown according to another embodiment. As an option, the present method 500 may be implemented in conjunction with features from any other embodiment listed herein, such as those described with reference to the other FIGS. Of course, this method 500 and others presented herein may be used to form structures for a wide variety of devices and/or purposes, which may or may not be related to the illustrative embodiments listed herein. It should be noted that the method 500 may include more or less steps than those described and/or illustrated in FIG. 5, according to various embodiments. It should also be noted that that the method 500 may be carried out in any desired environment.

As shown in FIG. 5, enzymatic reactive components 502 may be directly incorporated in a block copolymer network 504 prior to or after cross-linking said network. As described herein, each enzymatic reactive component 502 may be independently selected from an isolated enzyme, an enzyme comprising a cell fragment (e.g., a cell membrane or cell membrane fragment), and a liposome comprising/coupled to an enzyme. In some approaches, the enzymatic reactive component 502 may include at least one of: formate dehydrogenase, carbonic anhydrase, cytochrome p450, hydrogenase, particulate methane monooxygenasae (pMMO), photosynthetic complexes, etc.

As shown in the non-limiting embodiment of FIG. 5, the block copolymer network 504 is a di-block copolymer network comprising two different polymers (polymer A 506 and polymer B 508). In preferred approaches, polymer A 506 may comprise one or more reactant permeable, hydrophobic polymeric materials, whereas polymer B 508 may comprise one or more product permeable, hydrophilic polymeric materials. It is again important to note that while the block copolymer network 504 shown in FIG. 5 includes two phases (i.e., polymer A 506 and polymer B 508), said block copolymer network may include more than two phases in other approaches.

In various approaches, the enzymatic reactive components 502 may be incorporated directly into the block copolymer network 504 using lipopolymers (preferably di-block lipopolymers). Lipopolymers may be generated by linking a lipid to a polymer of interest, such as PEG, creating PEG-lipid conjugates, such as PEG-phosphatidylethanolamie. The lipid region of the polymer may spontaneously insert into the cell membrane, thereby creating a polymer functionalized liposome.

Figure 6:
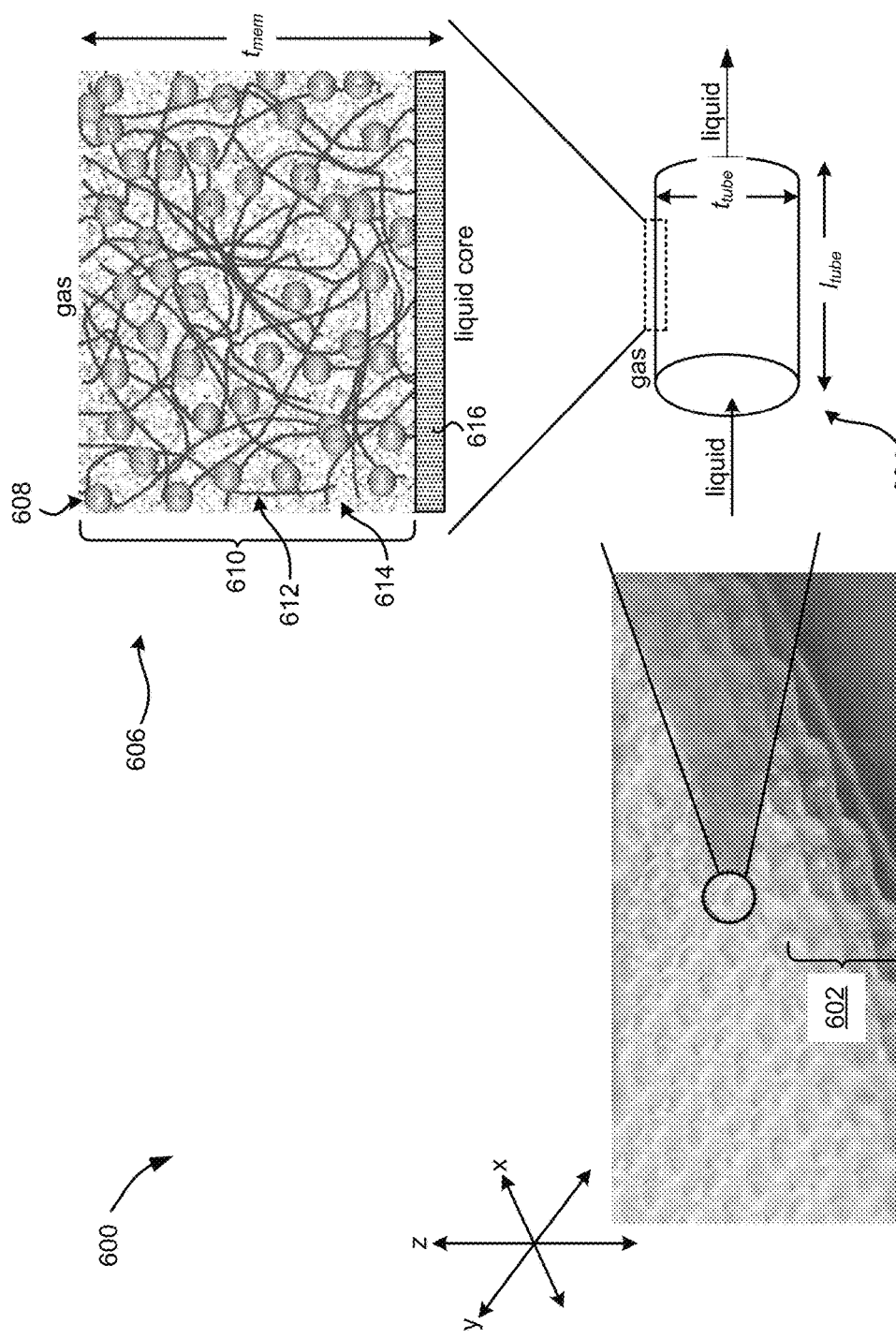
FIG. 6 is schematic representation of a bioreactor comprising a hollow tube network/lattice configured to optimize mass transfer, according to one embodiment.

Referring now to FIG. 6, a bioreactor 600 comprising a network/lattice of three dimensional structures configured to optimize mass transfer is shown according to one embodiment. As an option, the bioreactor 600 may be implemented in conjunction with features from any other embodiment listed herein, such as those described with reference to the other FIGS. Of course, the bioreactor 600 and others presented herein may be used in various applications and/or in permutations which may or may not be specifically described in the illustrative embodiments listed herein. For instance, the bioreactor 600 may be used in any desired environment and/or include more or less features, layers, etc. than those specifically described in FIG. 6.

As noted above, the bioreactor 600 includes a network/lattice 602 of three dimensional structures. As particularly shown in FIG. 6, the network/lattice 602 includes multiple layers (e.g., 2, 3, 4, 5, 6, 7, or more layers, etc.) of three-dimensional (3D) hollow tubes 604. It is important to note, however, that the hollow tube network/lattice 602 of the bioreactor 600, and others disclosed herein, may include one or more layers of three-dimensional hollow tubes 604 in various approaches. The hollow tubes 604 may preferably be oriented in the lattice such that their hollow interiors are perpendicular to a thickness direction of the lattice (e.g., perpendicular to the z axis shown in FIG. 6).

In some approaches, the bioreactor 600 may have a thickness (as measured parallel to the z-axis in FIG. 6) in a range from about 1 to about 300 cm, and a length (as measured in a direction parallel to the y-axis of FIG. 6) and width (as measured in a direction parallel to the x-axis of FIG. 6) scaled to the application, ranging from about 2 cm for laboratory applications to 10 meters for industrial applications.

The walls of each hollow tube 604 may comprise a membrane material 606, such as the membrane material of FIG. 3, configured to separate reactants (e.g., gaseous reactants) and products (e.g., hydrophilic products). Accordingly, the hollow tubes 604 form polymer microchannels through which the hydrophilic reaction products may flow.

As particularly shown in FIG. 6, the membrane material 606 of each hollow tube 604 may comprise a plurality of enzymatic reactive components 608 (e.g., isolated enzymes, membrane-bound enzymes, liposomes comprising/couple to an enzyme, etc.) embedded throughout a polymer network 610. The polymer network 610 may comprise reactant permeable fibrils of a first polymer 612 that increase the local concentration of reactants and enhance mass transfer throughout the membrane material 606. In some approaches, the enzymatic reactive components 608 may be immobilized on the fibrils of the first polymer 612. The polymer network 610 may also include at least another polymer material (e.g., a hydrogel matrix material) configured to hydrate the enzymatic reactive components 608 and provide a route for hydrophilic product removal. The membrane material 606 may also include an optional reactant permeable (product impermeable) layer 614 coupled to one side (e.g., an exterior side) of the polymer network 610 and/or a product permeable (reactant impermeable) layer 616 coupled to the opposite side (e.g., an interior side) of the polymer network 610. The optional product permeable (reactant impermeable) layer 616 may also facilitate product removal and prevent coenzyme and/or cofactor diffusion into the liquid core that contains the desired products.

The thickness, $t_{mem}$, of the membrane material 606 may be in a range from about 10 to about 1000 micrometers. In some approaches, $t_m$ may be about 300 μm. Additionally, The thickness, $t_{tube}$, of each hollow tube 604 may be in a range from about 10 micrometers to about 10 millimeters. In various approaches, $t_{tube}$ may be about 1 mm. In yet more approaches, the length, $l_{tube}$, of each hollow tube 604 may be in a range from about 5 centimeters to about 10 meters.

It is important to note that while the cross section of each hollow tube 604, as taken perpendicular to the y-axis of FIG. 6, is shown a circular, this need not be the case. For instance, in other approaches, each hollow tube 604 may have a cross sectional shape that is elliptical, rectangular, square, triangular, irregular shaped, etc. Moreover, in preferred approaches, each hollow tube 604 may have the same cross sectional shape, materials, and/or dimensions; however, this again need not be case. For instance, in alternative approaches, at least one of the hollow tubes 604 may have a cross sectional shape, materials, and/or dimensions that are different than that of another of the hollow tubes 604.

In one particular approach, one or more of the hollow tubes 604 in at least one of the layers may differ from one or more hollow tubes 604 in at least another of the layers with respect to: cross sectional shape, and/or one or more membrane material(s), and/or one or more dimensions. In another particular approach, one or more of the hollow tubes 604 in at least one of the layers may differ from at least another hollow tube 604 in the same layer with respect to: cross sectional shape, and/or one or more membrane materials, and/or one or more dimensions.

In yet further approaches, the spacing between the hollow tubes 604 in at least one of the layers may be about uniform. In more approaches, the spacing between the hollow tubes 604 in at least one of the layers may vary throughout the layer. For example, in one such approach, at least one of the layers may have at least one area having an average spacing, $s_1$, between adjacent hollow tubes 604, and at least a second area having an average spacing $s_2$, where $s_1$ and $s_2$ are different. In yet other approaches, the spacing between the hollow tubes 604 in at least one of the layers may differ from the spacing between the hollow tubes 604 of at least another of the layers.

Referring now to method 7, an exemplary method 700 of forming a bioreactor (such as those disclosed herein) is shown, according to one embodiment. As an option, the present method 700 may be implemented in conjunction with features from any other embodiment listed herein, such as those described with reference to the other FIGS. Of course, the method 700 and others presented herein may be used in various applications and/or in permutations, which may or may not be specifically described in the illustrative embodiments listed herein. Moreover, more or less operations than those shown in FIG. 7 may be included in method 700, according to various embodiments. Furthermore, while exemplary processing techniques are presented with respect to FIG. 7, other known processing techniques may be used for various steps.

Figure 7:
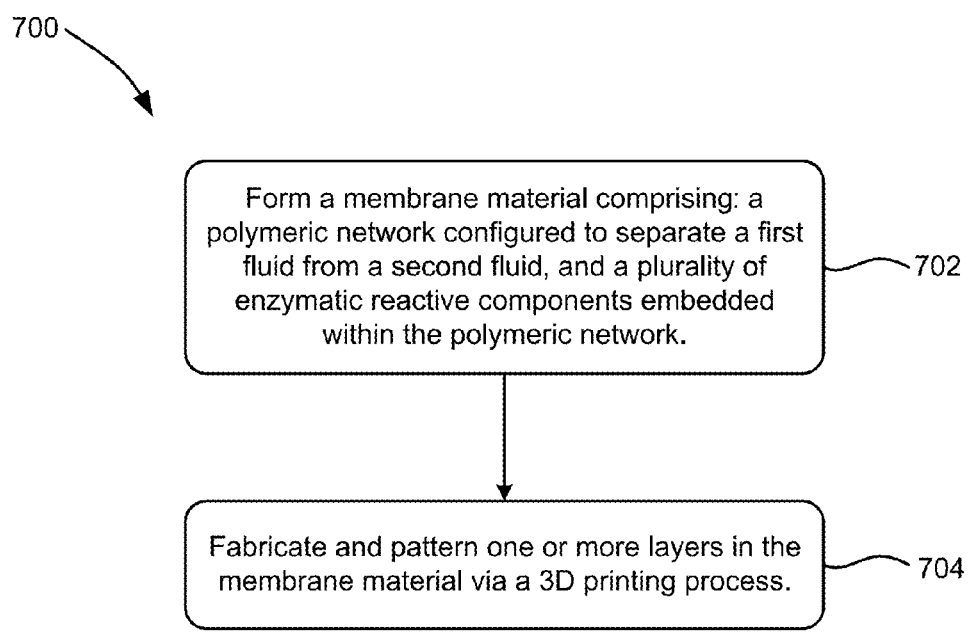
FIG. 7 is a flowchart of a method for forming a bioreactor via 3D printing, according to one embodiment.

As shown in FIG. 7, the method 700 includes forming a membrane material comprising: a polymeric network configured to separate a first fluid from a second fluid, and a plurality of enzymatic reactive components embedded/incorporated within the polymeric network. See operation 702.

The enzymatic reactive components may comprise any of the enzymatic reactive components disclosed herein including, but not limited to, isolated enzymes, trans-cell-membrane enzymes, cell-membrane-bound enzymes, liposomes coupled to/comprising an enzyme, combinations thereof, etc. Moreover, as discussed previously, the enzymatic reactive components may be embedded/incorporated into the polymeric network via several methods including, but not limited to: attaching the enzymatic reactive components to electrospun fibers of a first polymer, and backfilling with a second polymer (see, e.g., the method described in FIG. 4); directly incorporating the enzymatic reactive component into a polymer or block-copolymer network before or after crosslinking the network (see, e.g., the method described in FIG. 5); and other suitable incorporation methods as would become apparent to one having skill in the art upon reading the present disclosure.

The polymeric network may include any of the materials, and/or be of the same form, as any of the polymeric networks disclosed herein. For instance, this polymer network may be configured to serve as a mechanical support for the enzymatic reactive components embedded therein, as well as include nanometer scale domains of higher permeability to the first fluid and nanometer scale domains of higher permeability to the second fluid. Moreover, in some approaches, the polymeric network may include at least a two phase polymer network, e.g. a polymer network comprising two or more polymeric materials. In other approaches, the polymeric network may include a mixture of at least one polymer material and at least one inorganic material.

As indicated above, the polymeric network may be configured to separate a first and second fluid associated with a reaction catalyzed by the enzymatic reactive components embedded therein. The first and second fluids may be two different fluids, such as liquids and gasses, an aqueous species and a non-aqueous species, a polar species and a non-polar species, etc.

Figure 8:
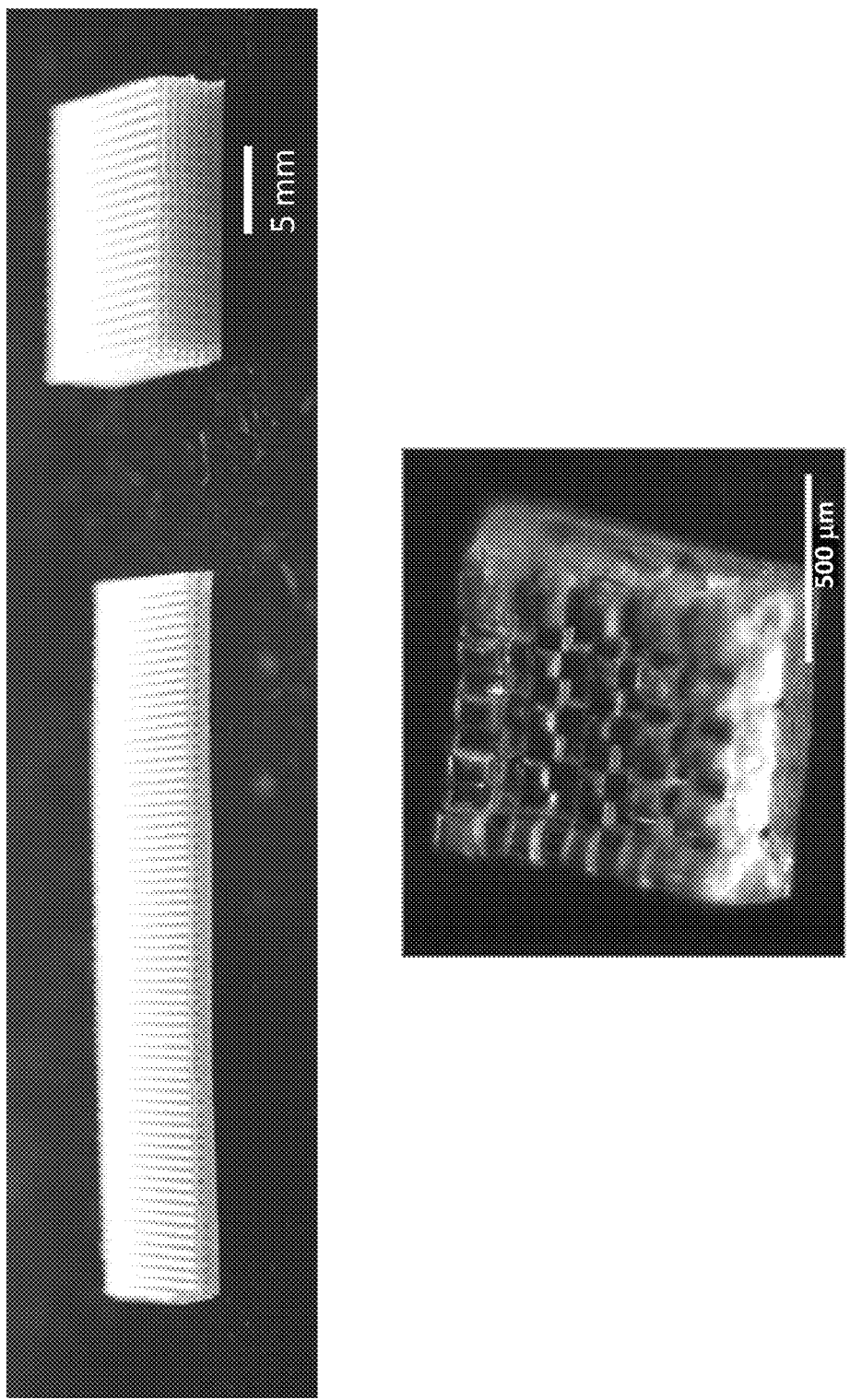
FIG. 8 illustrates various photographs of PEG-pMMO 3D structures formed/patterned according to a projection microstereolithography (PμSL) process, according to some embodiments.

As also shown in FIG. 7, the method 700 includes fabricating and patterning one or more layers in the membrane material via a 3D printing process. See operation 704. In preferred approaches, the 3D printing process includes a projection microstereolithography (PμSL) process as known in the art. In various approaches, each layer in the membrane material patterned/formed via the desired 3D printing process may include a plurality of three dimensional structures (e.g., hollow fibers, micro-capsules, hollow tube lattices, spiral wound sheets, etc.) configured to optimize the bioreactor geometry (and surface area) for mass transfer, reaction rate, product removal, continuous processing, etc. Photographs of several exemplary PEG-pMMO 3D structures formed/patterned according to a PμSL process are shown in FIG. 8.

As discussed in greater detail below, the novel bioreactors described herein, such as described in FIG. 6, may be particularly configured for methane activation with an energy efficiency from greater than or at least equal to about 68%. In such an approaches, the enzymatic reactive components embedded within the polymeric network may include pMMO to covert methane reactants, $CH_4$, to methanol products, $CH_3OH$. Preferably, this engineered pMMO may exhibit a specific activity greater than about 5 μm/(g·s) and/or a turnover frequency greater than about 10/s. Additionally, the amount of the engineered pMMO in such bioreactors may be about 50 g per L of reactor volume.

In some approaches, the aforementioned engineered pMMO may require a reducing agent for methane conversion. However, in other approaches, the engineered pMMO may not need such a reducing agent, or be configured to accept electrons via direct electron transfer. For instance, as shown in Table 1, the methane conversion may proceed by: (1) using pMMO configured to use methane as a reducing agent (reaction 1); (2) supplying electrons directly to the pMMO (reaction 2); and (3) using $H_2$ gas. Yet another reaction pathway may involve steam reformation as shown in reaction 3.

TABLE 1

| Reaction Pathway | Energy efficiency | Carbon efficiency |
|---|---|---|
| Reaction 1: $2CH_4 + O_2 \rightarrow 2CH_3OH$ | 80% | 100% |
| Reaction 2: $CH_4 + O_2 + 2H^+ + 2e^- \rightarrow CH_3OH + H_2O$ | >65% | 100% |
| Reaction 3: $4CH_4 + 3O_2 \rightarrow 3CH_3OH + CO + 2H_2O$ | 68% | 75% |

EXPERIMENTS/EXAMPLES

The following experiments and examples pertain to various non-limiting embodiments of the bioreactors described herein. In particular, the following experiments and examples are directed to bioreactors comprising pMMO embedded in a polymeric network for the conversion of methane to methanol. It is important to note that the following experiments and examples are for illustrative purposes only and do not limit the invention in anyway. It should also be understood that variations and modifications of these experiments and examples may be made by those skilled in the art without departing from the spirit and scope of the invention.

Overview

Advances in oil and gas extraction techniques have made vast new stores of natural gas (composed primarily of methane) available for use. However, substantial quantities of methane are leaked, vented, or flared during these operations. Indeed, methane emissions contribute about ⅓ of current net global warming potential. Compared to other hydrocarbons, and especially compared to the oil that is co-produced in hydrofracturing operations, methane has a much lower market value due to difficulty in methane storage and transport, and because methane has limited use as a transportation fuel.

Conversion of methane to methanol via conventional industrial technologies, such as steam reformation followed by the Fischer-Tropsch process, operate at high temperature and pressure, require a large number of unit operations, and yield a range of products. Consequently, conventional industrial technologies have a low efficiency of methane conversion to final products and can only operate economically at very large scales. There is thus a need in the art for a technology to efficiently convert methane to other hydrocarbons, and particularly to convert "stranded" sources of methane and natural gas (sources that are small, temporary, or not close to a pipeline) to liquids for later collection.

The only known true catalyst (industrial or biological) to convert methane to methanol under ambient conditions with 100% selectivity is the enzyme methane monooxygenase (MMO), found in methanotrophic bacteria, which converts methane to methanol according to the following reaction:

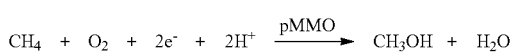

$$CH_4 + O_2 + 2e^- + 2H^+ \xrightarrow{pMMO} CH_3OH + H_2O$$

Partial methane oxidation by MMO enzymes can be carried out using whole methanotroph organisms, but this approach inevitably requires energy for upkeep and metabolism of the organisms, which reduces conversion efficiency. Moreover, biocatalysis using whole organisms is typically carried out in low-throughput unit operations, such as a stirred tank reactor.

One industrial-biological approach may therefor include separating the MMO enzyme from the host organism. Isolated enzymes may offer the promise of highly controlled reactions at ambient conditions with higher conversion efficiency and greater flexibility of reactor and process design. MMOs have been identified in both soluble MMO (sMMO) and particulate (pMMO) form. The use of pMMO has advantages for industrial applications because pMMO comprises an estimated 80% of the proteins in the cell membrane, Moreover, concentrating pMMO to a reasonable purity requires only isolating the membrane fraction of the lysed cells using centrifugation.

Traditional methods of enzyme immobilization and exposure to reactants are not sufficient to use pMMO effectively. These typical methods include cross-linking enzymes or immobilizing them on a solid support so that they can be separated from the products and carrying out batch reactions in the aqueous phase in a stirred tank reactor. As discussed previously, operation of a stirred tank reactor has several drawbacks, including low productivity, high operating costs, loss of catalytic activity due to enzyme inactivation, and variability in the quality of the product. The stirred-tank reactor is also not the optimal design for gas to liquid reactions such as methane to methanol conversion, as it does not allow efficient delivery of reactant gases to enzymes or organisms in the bulk solution. Gas delivery in stirred tank reactors is often achieved by bubbling the gas through the liquid, but this approach suffers from mass-transfer limitations. Furthermore, methane and oxygen are only sparingly soluble in aqueous solvents: 1.5 mM/atm and 1.3 mM/atm respectively at 25° C. Reactant concentrations are necessarily solubility-limited when the enzymes or organisms are dispersed in the aqueous phase.

Moreover, another reason as to why the pMMO enzyme is not amenable to standard immobilization techniques designed for soluble proteins is due to the fact that surfactant solubilization of isolated pMMO leads to a pronounced reduction in activity. For example, high surface area porous inorganic supports have been extensively studied and implemented for immobilizing soluble enzymes, and have been shown to enhance enzyme stability while achieving high enzyme loading in nanometer scale pores. The majority of the surface area in mesoporous materials is accessible only to proteins significantly smaller than 50 nm, and would therefore be inaccessible to the large (>100 nm), optically opaque vesicles and liposomes that comprise pMMO in crude membrane preparations.

Accordingly, the exemplary embodiments discussed in this experimental section are directed toward advances in biocatalytic processes for selective methane conversion. For instance, said exemplary embodiments are particularly directed toward a biocatalytic material comprising pMMO embedded in polyethylene glycol diacrylate (PEGDA) hydrogel. Embedding enzymes, such as pMMO that operate on gas phase reactants within the solid, gas permeable polymer hydrogel allows tuning of the gas solubility, permeability, and surface area thereof. An additional advantage to immobilizing pMMO within the polymer hydrogel, rather than on the surface of an impermeable support, is the potential to fully embed pMMO throughout the depth of the polymer hydrogel for high loading. PEGDA was selected as the primary polymer substrate because of its biocompatibility and flexibility for further development. PEGDA may be physically or chemically combined with hydrophobic polymers in additional approaches for enhanced gas solubility and transport in various approaches. Moreover, the pMMO embedded PEGDA hydrogel is amenable to various forms of 3D-printing, which offers the ability to rapidly prototype structures, tune micron to centimeter-scale material architecture, and precisely tailor structures for the system configuration and mass transfer, heat, and diffusion limitations.

Results a. pMMO Activity in PEG Hydrogel

Several methods for embedding pMMO in a PEGDA based polymer hydrogel were explored to enable its use as a biocatalytic material which could be molded into controlled, predetermined structures with tunable permeability and surface area for practical use. Initial efforts focused on solubilizing the crude membrane preparations using surfactant so that the material could be incorporated homogeneously in the polymer. It was discovered that any contact of the crude membrane preparations with surfactant, including encapsulation in nanolipoprotein particles, led to a pronounced decrease in activity. However, mixing the crude membrane fractions, either as prepared or extruded as liposomes directly with low concentrations of PEGDA 575 gave promising results. According the experiments described in this section focused on optimizing the activity and protein retention of crude membrane preparations with PEGDA 575.

Figure 9:
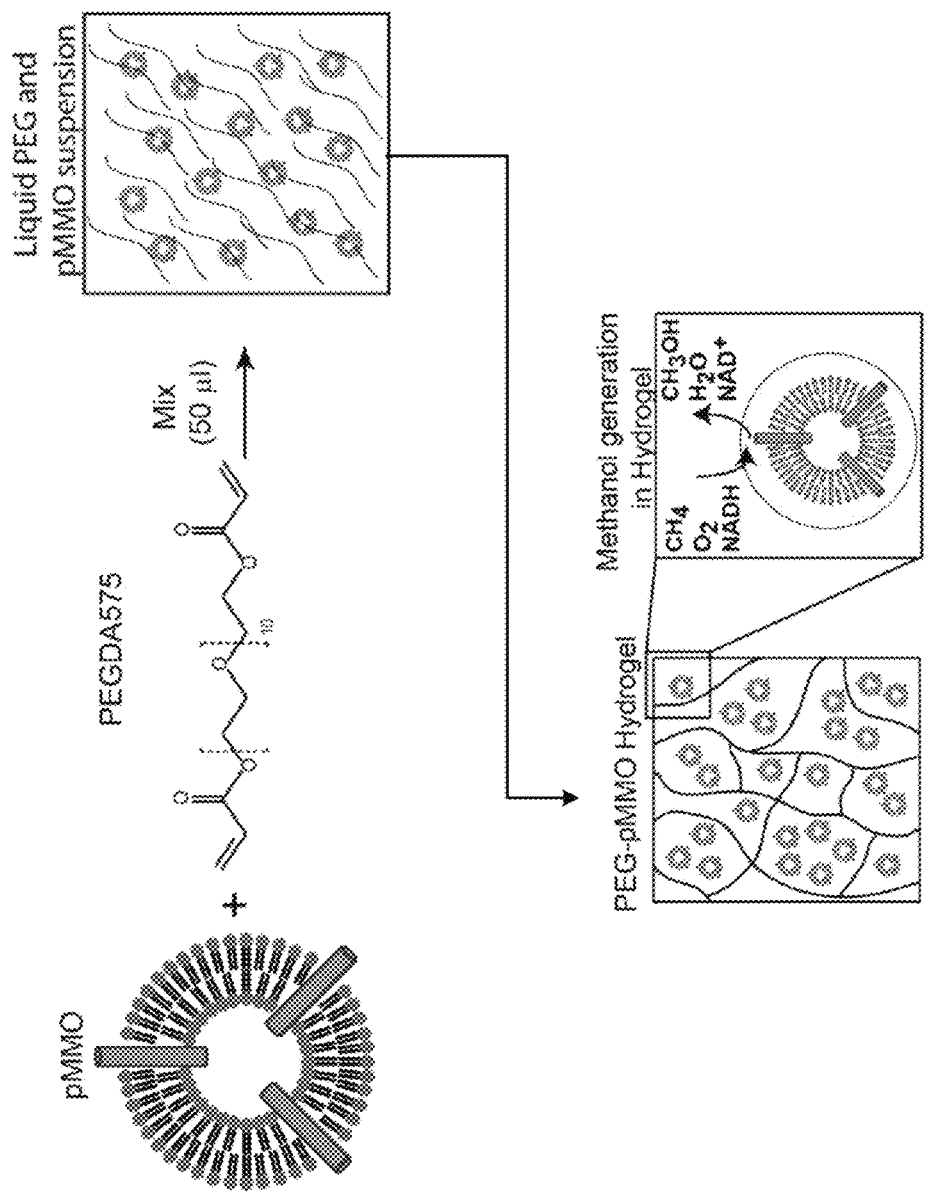
FIG. 9 is a process flow illustrating a method for forming a polyethylene glycol diacrylate (PEGDA) hydrogel comprising particulate methane monooxygenasae (pMMO), according to one embodiment.

A schematic of the method used to fabricate the PEG-pMMO hydrogels is shown in FIG. 9. The synthesis of the PEG-pMMO materials required only membrane bound pMMO, PEGDA macromer, photoinitiator (not shown), and ultraviolet (UV) light. Photoinitiator concentrations higher than 0.5 vol % in PEGDA decreased the pMMO activity, therefore the photoinitiator concentration was held constant at 0.5 vol %.

Membrane bound pMMO alone in each activity assay as a positive control. The measured activity of the membrane bound pMMO alone was highly variable from experiment to experiment, from about 75 to 200 nmol MeOH mg$^{-1}$ min$^{-1}$, while the optimized PEG-pMMO samples were less variable, in a range from 65 to 128 nmol MeOH mg$^{-1}$ min$^{-1}$. The measured activity for both membrane bound pMMO alone and immobilized pMMO are similar to known values for membrane bound pMMO with methane as a substrate: 25-130 nmol MeOH mg$^{-1}$ min$^{-1}$.

Figure 10A:
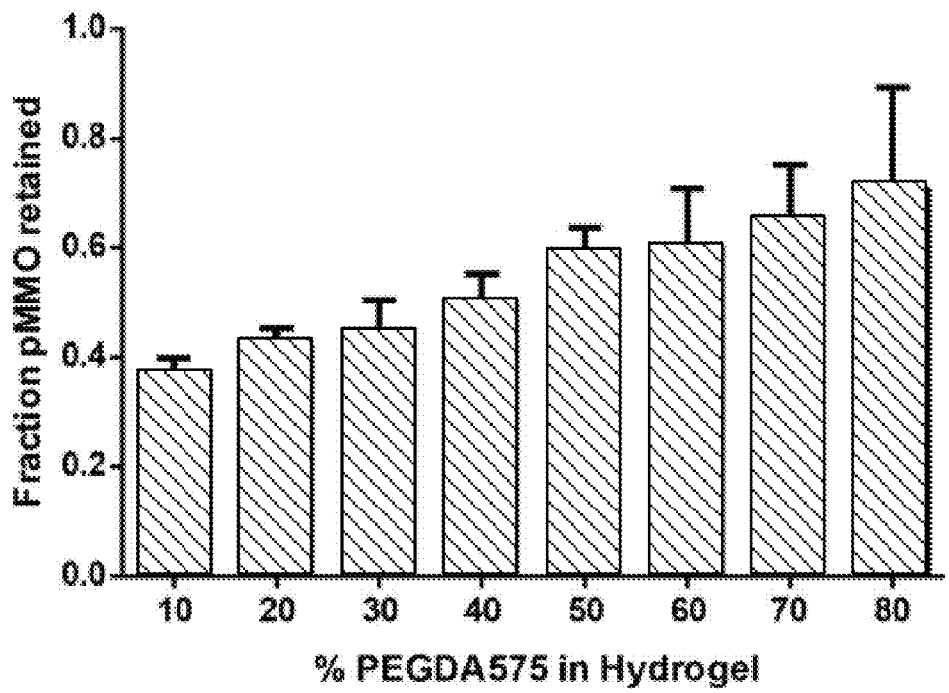
FIG. 10A is a plot illustrating pMMO retention by weight in a PEGDA hydrogel as a function of the volume percentage of PEGDA present during polymerization, where 150 μg of pMMO is initially included within the PEGDA hydrogel.
Figure 10B:
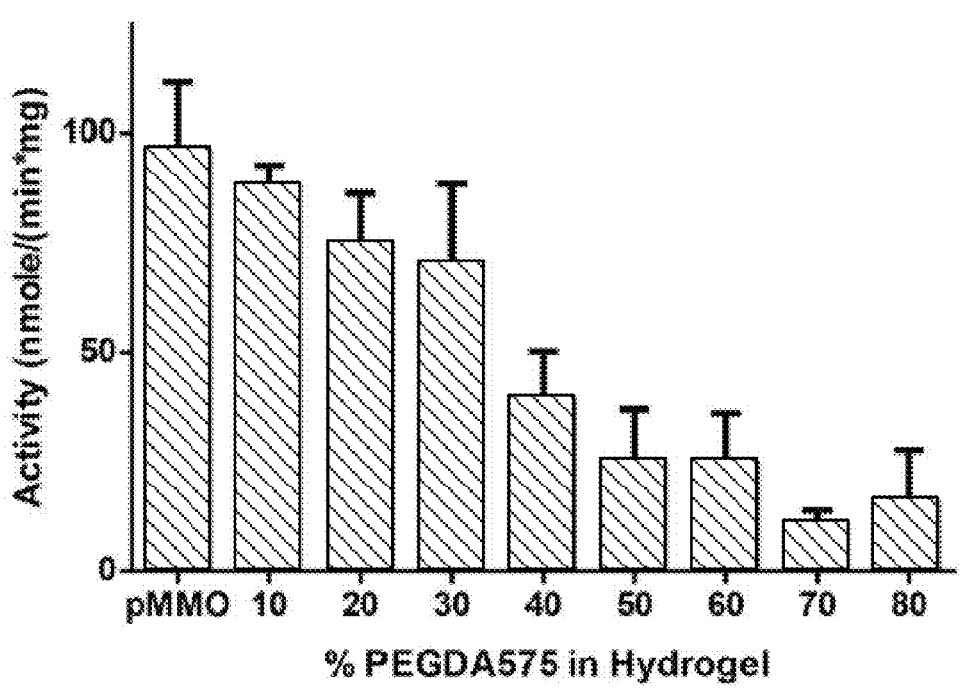
FIG. 10B is a plot illustrating pMMO activity in a PEGDA hydrogel as a function of the volume percentage of PEGDA present during polymerization, where 150 μg of pMMO is initially included within the PEGDA hydrogel.
Figure 10C:
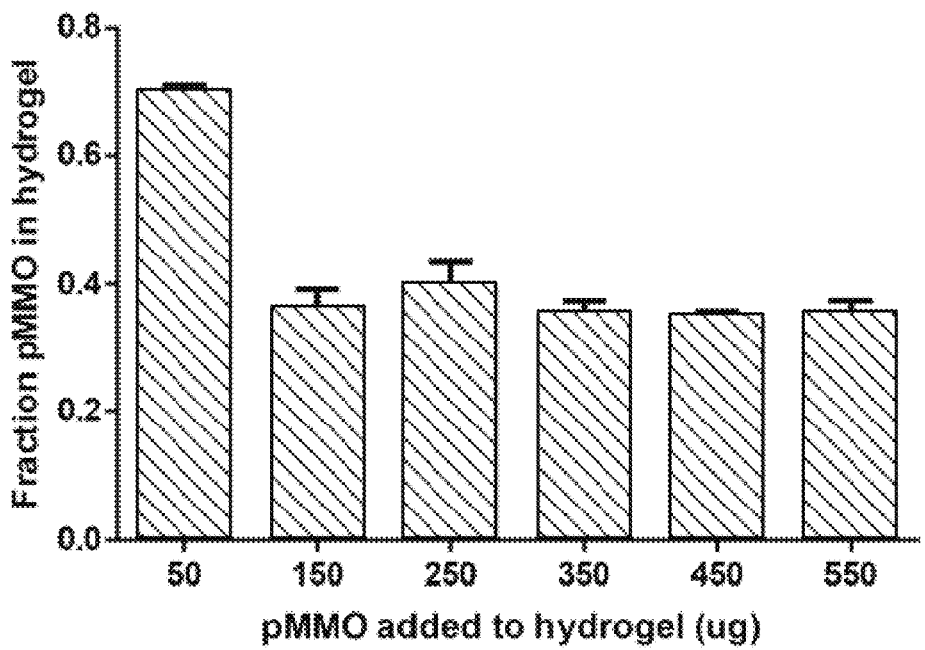
FIG. 10C is a plot illustrating pMMO retention by weight in a PEGDA hydrogel as a function of the amount of pMMO (μg) included during polymerization.
Figure 10D:
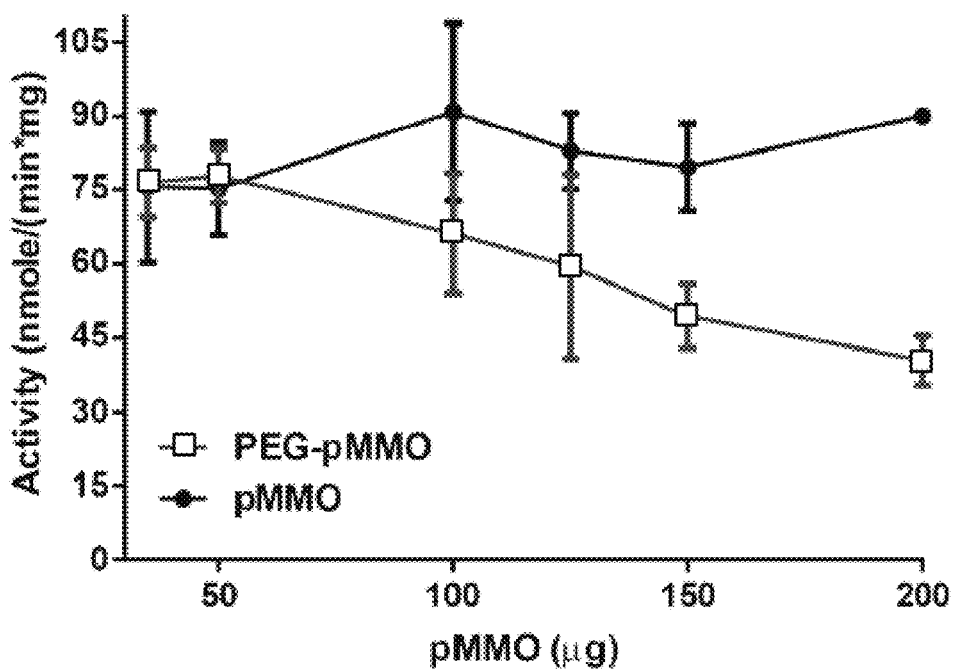
FIG. 10D is a plot illustrating the activity of PEGDA-pMMO and a pMMO control as a function of the amount of pMMO (μg) included during the activity assay.

FIGS. 10A-10D shows the results from systematically increasing the volume % of PEGDA in the solution prior to curing on protein retention (FIGS. 10A, 10C) and activity (FIGS. 10B, 10D). Mixing the pMMO solution with PEGDA at the appropriate vol % (10-80%), and UV curing resulted in 50 µl solid PEG-pMMO hydrogels. As the PEGDA vol % was increased from 10-80%, the overall stiffness of the material increased and the amount of residual liquid on the surface of the hydrogel decreased. A gradual increase was observed in the fraction of pMMO that was retained (0.4-0.75) when the PEGDA vol % was increased from 10-80% (FIG. 10A).

However, a dramatic decrease in pMMO activity was observed as the PEGDA vol % was increased (FIG. 10B). At 10% PEGDA, the pMMO activity was approximately 88+/-4 nmol MeOH min$^{-1}$mg$^{-1}$, which closely corresponded to the activity of pMMO alone (96+/-15 nmol MeOH min$^{-1}$mg$^{-1}$) (FIG. 10B). This value dropped below 30 nmol MeOH min$^{-1}$mg$^{-1}$ when the PEGDA vol % was greater than 50% (FIG. 10B). The amount of pMMO retained in the hydrogel before and after the activity assay did not change, indicating that no pMMO leached out during the activity assay and the enzyme was efficiently entrapped in the hydrogel. These combined findings demonstrate that one must consider both pMMO retention and activity when identifying the optimal PEGDA vol %. Since only a marginal increase in pMMO retention (0.4 vs 0.42) and a more significant decrease in pMMO activity (88 vs 74 nmol MeOH min$^{-1}$mg$^{-1}$) was observed when the PEGDA vol % was increased from 10% to 20%, all remaining experiments were performed using 10 vol % PEGDA.

FIGS. 10C and 10D illustrate the effect of varying the concentration of pMMO during hydrogel fabrication on pMMO retention and activity. For these experiments, the amount of pMMO used to generate the 50 µl PEG-pMMO hydrogel was varied between 50 µg and 550 µg. The fraction of pMMO retained was the highest at the lowest pMMO concentration tested (50 µg-0.75 retained) and a dramatic decrease was observed when the pMMO was increased to 150 µg (~0.4 retained) (FIG. 10A). Further changes in the total pMMO retained was not observed when the pMMO was increased up to 550 µg. To assess the effect of varying the pMMO concentrations in the PEG-pMMO hydrogel on activity, PEG-pMMO hydrogels were prepared with 50-550 µg of pMMO, which resulted in retention of 35-200 µg of pMMO in the hydrogel, and the activity was measured. As shown in FIG. 10B, pMMO activity in the hydrogel was similar to the activity of pMMO alone when the amount of pMMO retained was below 50 µg; however, there was a gradual decrease in pMMO activity in the hydrogels as the pMMO levels were increased from 50-200 µg, which was not observed in the pMMO alone sample (FIG. 10D).

Preserving the native activity of pMMO in the PEG hydrogel required a balance between pMMO loading and enzyme activity. Higher polymer concentrations gave rise to higher pMMO loading and retention (FIG. 10A). Increasing the polymer concentration also correlated with diminished pMMO activity. This trend may be due to reduced polymer permeability or enzyme degradation by acrylate groups and/or free radicals at higher polymer concentrations. While it has been shown that PEDGA concentration (and by correlation, crosslinking density) has minimal effect on methane permeability in the gas phase, gas permeability is affected by the hydration (swelling) of hydrogel materials. Thus, PEGDA concentration may impact methane permeability in swollen PEG-pMMO. Higher PEGDA concentrations also decrease the distance between crosslinks and the diffusion of aqueous solutes through the hydrogel. Therefore, higher PEGDA concentrations may limit diffusion of the NADH cofactor to the enzyme or diffusion of the methanol product from the active site. Additionally, photoinitiated cross-linking reaction used to generate the cross-linked hydrogel results in the generation of free radicals, which can result in the oxidation of amino acids in proteins and cleavage of peptide bonds. The optimized PEG-pMMO formulations described in the text were remarkable in that they preserved physiological pMMO activity in a polymeric material; if a higher protein or polymer content is required the above issues might be managed by changing the macromer length and/or curing chemistry, in order to increase hydrogel mesh size (promoting diffusion) and reduce the number of radicals generated.

b. Reuse and Stability of PEG-pMMO Hydrogels

Figure 11A:
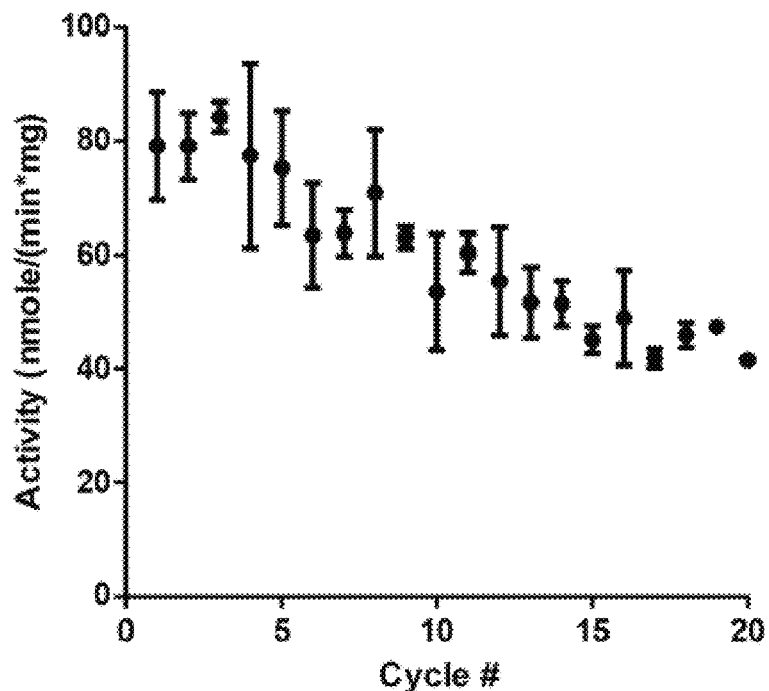
FIG. 11A is a plot illustrating the activity of the PEGDA-pMMO hydrogel after reusing said hydrogel over multiple cycles.
Figure 11B:
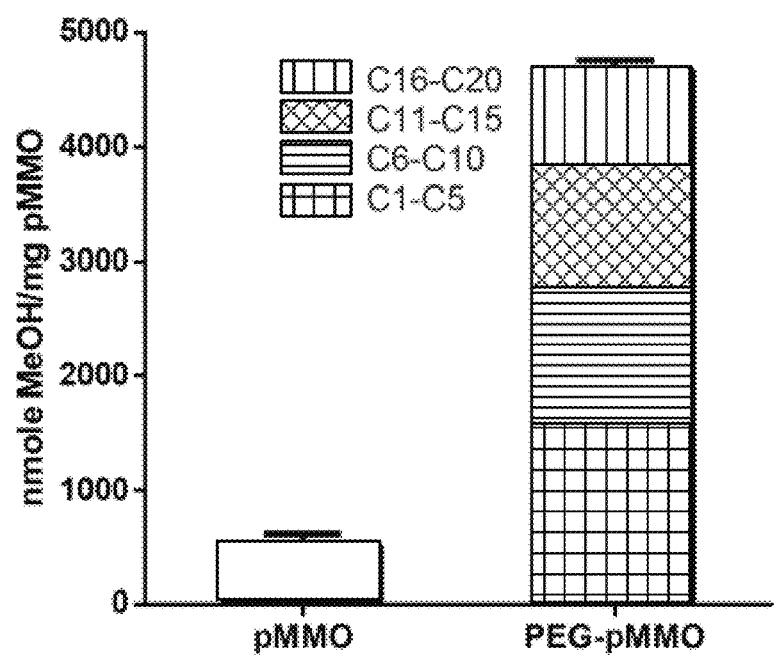
FIG. 11B is a plot illustrating the amount of methanol (nmoles) produced per mg of pMMO for both as-isolated membrane bound pMMO and PEGDA-pMMO over twenty cycles of methane activity assay.

The development of fully active pMMO in a polymer material allowed the reuse of pMMO without painstaking centrifugation with each new set of reactants. Measurements were made regarding the effects of reuse of the PEG-pMMO hydrogel on overall enzyme activity and methanol generation using PEG-pMMO that was prepared with an initial pMMO amount of 150 µg and 10 vol % pMMO (FIGS. 11A-11B). In these experiments, the PEG-pMMO hydrogels were subjected to 20 cycles of 4 min exposures to methane. The hydrogel was washed thoroughly between each cycle to ensure that no residual methanol product remained in the hydrogel between cycles. The protein content in the reaction buffer for each cycle was measured to verify that the pMMO concentrations remained constant, and that there was no leaching through the course of the study. As shown in FIG. 11A, the activity between assay cycles 1 to 5 remained close to the initial activity (~80 nmol MeOH min$^{-1}$mg$^{-1}$) and then gradually decreased to ~45 nmol MeOH min$^{-1}$mg$^{-1}$ after 20 cycles. The error bars correspond to the standard deviation from the average of four replicates. FIG. 11B shows the cumulative methanol produced from these 20 consecutive reactions of PEG-pMMO compared to a single reaction of membrane bound pMMO. Immobilization of fully active pMMO in a material allowed the facile production of 10 fold more methanol per protein than could be produced with membrane bound pMMO (which can only be reused with painstaking repeated centrifugation and rinsing steps).

c. Continuous Flow-through Bioreactor

Figure 12A:
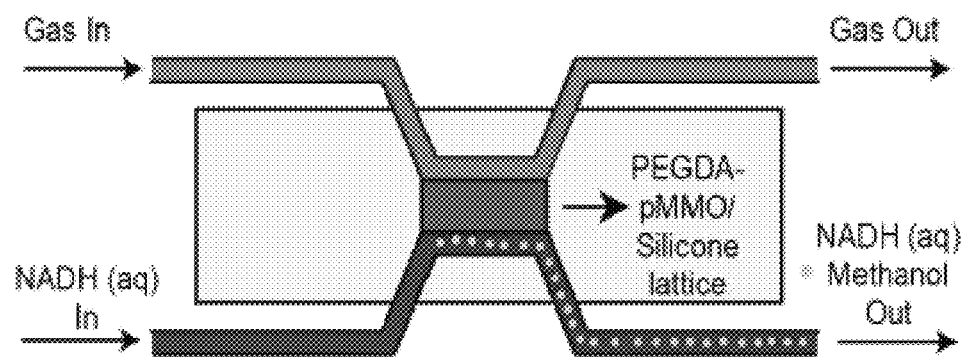
FIG. 12A is a schematic representation of a continuous flow-through PEGDA-pMMO hydrogel bioreactor, according to one embodiment.

Establishing that that the PEG-pMMO material could be reused with no measureable protein leaching indicated that the material would be amenable for use in a bench-scale continuous flow reactor. A design where the pMMO material is suspended between gas and liquid reservoirs was discovered herein as desirable given that pMMO acts upon gas phase reactants and generates liquid phase. However, PEG-pMMO, and hydrogels in general, are mechanically brittle and difficult to handle when molded as thin membranes. Accordingly, the PEG-pMMO material was embedded into a three dimensional silicone lattice (printed using Direct Ink Write) in order to greatly increase the mechanical stability and to easily tune the size and shape of the hydrogel for use in a continuous reactor (FIG. 12A). As discussed in greater detail below, the lattice was constructed of 250 micron silicone struts and contained 250 micron void spaces (50% porosity) which were then infilled with PEGDA 575, crude pMMO membrane preparations, and photoinitiator and crosslinked in place with ultraviolet light. Two such lattice structures, thin and thick, were designed to compare effects of PEG-pMMO surface area to volume ratio on methanol production. The surface area to volume ratio of thin vs. thick for these experiments was 5 to 1. The silicone lattice structure increases the bulk gas permeability of the materials, since silicone permeability is at least 50 times greater than the PEGDA hydrogel permeability.

Figure 12B:
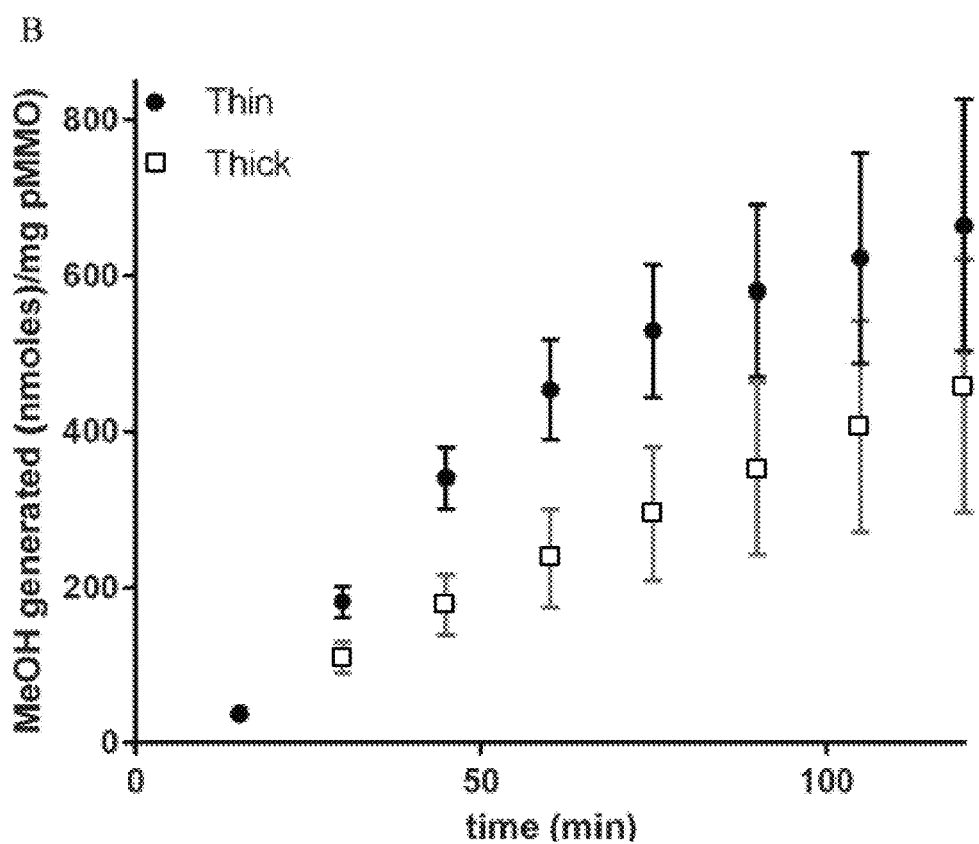
FIG. 12B is a plot illustrating the amount of methanol (nmole) produced per mg of pMMO in the PEGDA-pMMO hydrogel bioreactor of FIG. 12A.

The resulting hybrid silicone-PEG-pMMO lattice materials were mechanically robust, allowing the suspension of the PEG-pMMO lattice of 1 millimeter thickness between gas and liquid reservoirs in a flow-through reactor. A schematic of the reactor cross section is shown in FIG. 12A. With this configuration, a methane/air gas mixture was flowed on one side of the lattice and the NADH was introduced on the other side, while continuously removing and collecting methanol in buffer. In order to determine the length of time the membrane could be continuously used, the cumulative methanol produced per mg of enzyme was measured at 25° C. at 30 min intervals in the thick lattice over the course of 5.5 hours. The methanol production rate (slope of methanol vs. time curve) was stable for about 2.5 hours, and declined gradually over the next 3 hours. In order to evaluate whether the geometry of PEG-pMMO material influenced methanol production rates, reactor outlet fractions from reactors containing the thin and thick lattices were compared at 15 min intervals at 45° C. over the course of two hours (FIG. 12B) in triplicate. The methanol concentrations produced in the flow reactor were on average 12 and 6% of what was predicted, for thin and thick lattices, respectively, based upon analyte flow rates and an assumed pMMO activity of 80 nmol MeOH min$^{-1}$mg$^{-1}$. The low concentration values relative to predicted values may be due to lower actual pMMO concentrations in the material than was calculated. As shown in FIG. 12B, the methanol produced (per mg of protein) by the thin membrane was double that produced by the thick membrane over the course of the first hour. Over the following hour, the methanol production rate by the thin membrane declined relative to that of the thick membrane; after two hours the average total methanol produced by the thin membrane was 1.5 times higher than that produced by the thick membrane. The results demonstrate that the ability to tune the geometry of immobilized pMMO, even at the millimeter scale, impacts the performance of the biocatalytic material.

d. Direct Printing of PEG-pMMO Hydrogels

Projection microstereolithography (PμSL) allows three dimensional printing of light-curable materials by projecting a series of images on the material, followed by changing the height of the stage at discrete increments, with micron-scale resolution in all three dimensions. Therefore, it was an ideal technique for directly printing the PEG-pMMO material and determining whether changing geometrical features of the material at these length scales can influence activity. PμSL was thus used to print PEG-pMMO lattice structures with increased surface area to volume ratio due to 100 μm$^2$ vertical channels corresponding to ~15% void volume. In this experiment, the pMMO concentration of 5 mg/ml did not attenuate the light enough for highest resolution printing; consequently feature resolution was reduced in the z-direction and each layer of printed pMMO was exposed to multiple exposures to UV light. The pMMO activity in the printed cubic lattices with a total volume of about 27 mm$^3$, which took approximately 50 min to print using PμSL, was reproducible but modest at 29 nmol MeOH min$^{-1}$mg$^{-1}$. The reduction in activity compared to crude pMMO is likely due to the duration of the printing at room temperature as well as the overexposure of pMMO to UV during curing. However, the cubic lattices retained about 85% of the enzyme based on the solid volume of the lattice (23 mm$^3$) corresponding to the highest protein loading that was have achieved. While not wishing to be bound by any theory, it is thought that this high retention was likely due to higher cross-linking efficiency.

Figure 13:
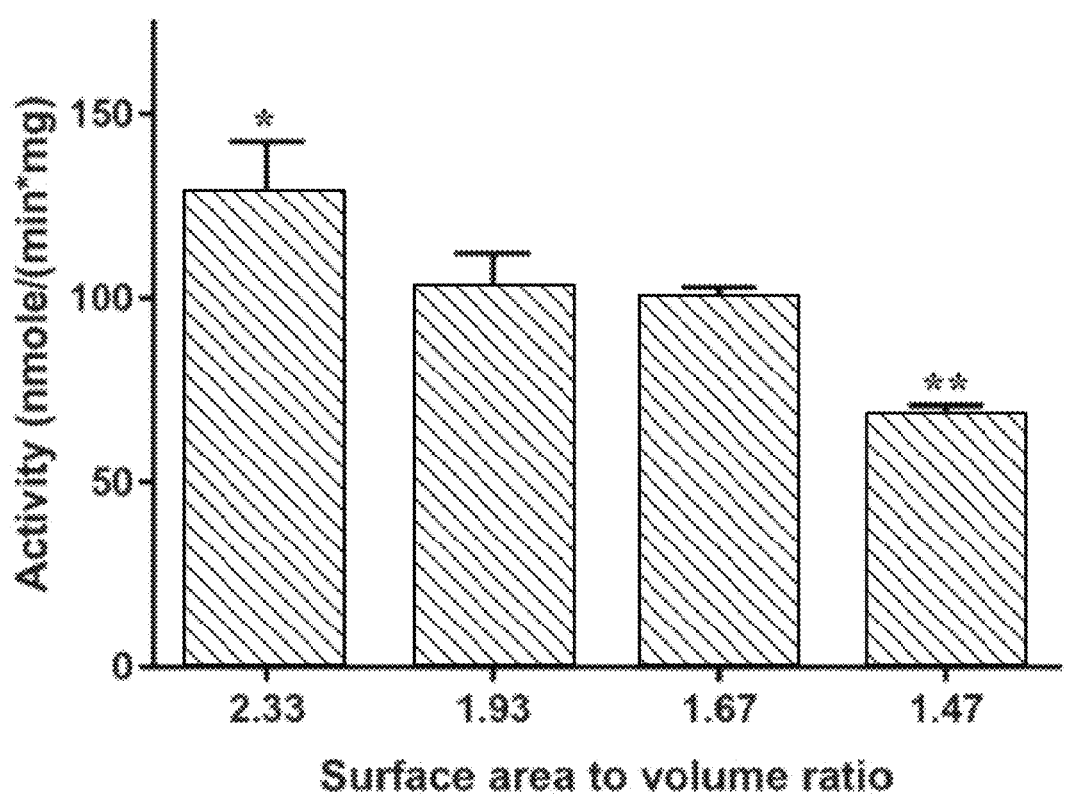
FIG. 13 is a plot illustrating the dependence of PEGDA-pMMO activity on surface area to volume ratio for a PEGDA-pMMO hydrogel bioreactor.

Since the lattice geometry did not permit precise tuning of surface area to volume ratios, due to bending of lattice struts under water surface tension, a different PμSL tool designed to generate larger parts was used to print solid and hollow PEG-pMMO cylinders with surface area to volume ratios ranging from 1.47-2.33 and diameters ranging from of 1-5 mm. The hollow tube geometry may allow more facile diffusion of reactants because both the inner and outer surfaces of the cylindrical materials would be exposed. The total print time for an array of cylinders using the large-area PμSL tool was significantly reduced to ~1 min by eliminating z-axis resolution, and the pMMO concentration was reduced to 2.3 mg/ml to allow UV light penetration through the 1.5-3 mm depth of the resin. Remarkably, the activity of pMMO in the hydrogels increased with greater surface area to volume ratios as shown in FIG. 13, with the highest ratio of 2.33 resulting in an average activity of 128+/−14 nmol MeOH min$^{-1}$mg$^{-1}$ per cylinder, which corresponds to the highest reported physiological activity of membrane bound pMMO. The cylinders of the lowest ratio, 1.47, had an average pMMO activity of 67+/−3 nmol MeOH min$^{-1}$mg$^{-1}$. It should also be noted that the cylinders with the lowest surface area to volume ratio were only 1.5 mm in height and therefore completely submerged in the liquid phase during the activity assay, whereas all other cylinders tested were 3 mm in height and only partially submerged during the assay. Hydrogels protruding from the liquid allowed a direct interface between the gas phase and PEG-pMMO. This exposed interface likely increased the methane concentration in the PEG-pMMO material since the solubility of methane in PEG is several times higher than that in water. On average, 38% of the protein was encapsulated, although it was variable depending on the dimensions of each cylinder (27-54%). These results, combined with the results from the continuous flow reactor, indicate that an optimal pMMO material design may be hierarchical, with the smallest feature sizes at the micron scale.

Specific Methods a. Materials

Reagents for buffers (PIPES, NaCl, and NaOH), HPLC grade methanol (≥99.9% purity), polyethylene glycol diacrylate 575 (PEGDA 575), and the cross-linking initiator, 2-hydroxy-2-methylpropiophenone (Irgacure® 1173), was purchased from Sigma-Aldrich (St. Louis, Mo.). All reagents were used as received. Methane gas (99.9% purity) was obtained from Matheson Tri-gas, Inc. (Basking Ridge, N.J.). pMMO concentrations were measured using the DC™ protein assay purchased from Bio-Rad (Hercules, Calif.). Lithium phenyl-2,4,6-trimethylbenzoylphosphinate (LAP) photoinitiator was synthesized following a procedure known in the art.

b. pMMO: Cell Growth and Membrane Isolation

*Methylococcus capsulatus* (Bath) cells were grown in 12-15 L fermentations. *M. capsulatus* (Bath) cells were grown in nitrate mineral salts medium (0.2% w/v KNO$_3$, 0.1% w/v MgSO$_4$.7H$_2$O and 0.001% w/v CaCl$_2$.2H$_2$O) and 3.9 mM phosphate buffer, pH 6.8, supplemented with 50 μM CuSO$_4$.5H$_2$O, 80 μM NaFe(III) EDTA, 1 μM Na$_2$MoO$_4$.2H$_2$O and trace metals solution. Cells were cultured with a 4:1 air/methane ratio at 45° C. and 300 rpm. Cells were harvested when the A$_{600}$ reached 5.0-8.0 by centrifugation at 5000×g for 10 min. Cells were then washed once with 25 mM PIPES, pH 6.8 before freezing in liquid nitrogen and storing at −80° C. Frozen cell pellets were thawed in 25 mM PIPES, pH 7.2, 250 mM NaCl buffer (herein referred to as pMMO buffer) and lysed by microfluidizer at a constant pressure of 180 psi. Cell debris was then removed by centrifugation at 20,000-24,000×g for one hr. The membrane fraction was pelleted by centrifugation at 125,000×g for one hour and washed 3 times with pMMO buffer before freezing in liquid nitrogen and storing at −80° C. Final protein concentrations were measured using the Bio-Rad DC™ assay. Typical storage concentrations ranged from 20-35 mg/ml.

c. Formation of the PEG-pMMO Hydrogels

Prior to preparation of the PEG-pMMO hydrogels, frozen as-isolated crude membranes from *M. Capsulatus* (Bath) (herein referred to as membrane-bound pMMO) was thawed at room temperature and used within 5 hours of thawing. Thawed membrane-bound pMMO (50-500 μg) was then mixed with PEGDA 575 in pMMO buffer at room temperature to form liquid PEG and pMMO suspensions having a final volume of 50 μl and 10-80 (v/v %) PEGDA 575. A photoinitiator (not shown in FIG. 9) was included in the suspension at 0.5 vol % with respect to PEGDA 575. The suspension was mixed by pipetting to homogeneity and then transferred to a 1 ml syringe with the tip removed. The syringe was then immediately placed under UV light at 365 nm, 2.5 mW/cm$^2$ intensity, for 3 min. After the UV exposure, the 50 µl PEG-pMMO hydrogel block was slowly pushed out of the syringe onto a kimwipe where it was gently blotted and then rinsed twice in pMMO buffer to remove unreacted reagents.

d. Activity Assay

All reactions were carried out in 2 ml glass reaction vials in pMMO buffer with 6 mM NADH as a reducing agent. Vials with 50-500 µg pMMO in 125 µl buffer solution were used as controls. For the immobilized enzyme samples, each 50 µl PEG-pMMO hydrogel block was placed in a vial and partially submerged in 75 µl buffer solution immediately after curing and rinsing. 1 ml of headspace gas was removed from each vial using a 2 ml gas tight glass syringe and replaced with 1 ml of methane, then the reaction vial was immediately placed in a heating block set at 45° C. and incubated for 4 min at 200 rpm. After 4 min, the samples were heat inactivated at 80° C. for 10 min. Samples were then cooled on ice for 20 min and pMMO control vials were centrifuged to remove the insoluble membrane fraction. For the cyclic activity assays using the PEG-pMMO immobilized enzyme, the reaction was stopped by opening and degassing the head space and immediately removing the solution for GC analysis. The block was then rinsed three times with 1 ml of pMMO buffer per wash and the assay was repeated. The amount of methanol generated during the reaction was measured by gas chromatography/mass spectrometry (GC/MS) analysis using an Agilent Pora-PLOT Q column and calibration curves were generated from methanol standards.

e. pMMO Flow Reactor

A simple cubic polydimethyl siloxane (PDMS) lattice with 250 micron struts and 250 micron spacing was printed using Direct Ink Write as described to provide methane permeability throughout the PEG material and to provide mechanical support. A top layer of 50 micron thick PDMS was fabricated by spin-coating Dow Corning SE-1700 PDMS diluted in toluene on a hydrophobized silicon wafer. This thin PDMS membrane prevented leakage of liquid through the membrane but provided gas permeability. Two different flow cell geometries were fabricated using polycarbonate plastic: a flow cell for a higher surface area, thin lattice (1.25 cm wide by 3 cm long) and a lower surface area, thick lattice, 1.25 by 1.25 cm. The thin lattice was 6 layers thick, and the thick lattice had 16 layers. The lattices were made hydrophilic by treating them in air plasma for 5 minutes followed by storage in deionized water. To incorporate the pMMO into the lattices, a 10 vol % concentration of PEGDA 575 was mixed with crude pMMO membrane preparations to a final concentration of 5 mg/ml pMMO. Two hundred microliters of the pMMO/PEGDA mixture were pipetted into the lattice and cured with 365 nm UV light at 2.5 mW/cm$^2$ intensity for 4 min, forming the mixed polymer (PEG/PDMS) membrane. The final concentration of pMMO in the lattices was calculated, rather than directly quantified using a protein assay, due to difficulties in quantifying the material in the lattice. The membrane was then loaded into the cell and rinsed with buffer to remove any unpolymerized material. The flow cell was placed on a hot plate calibrated with thermocouple so that the membrane would reach either 25 or 45 degrees ° C. An NADH/buffer solution (4 mg/ml NADH in PIPES pH 7.2) was prepared as the liquid phase in a 5 ml syringe, and the gas phase was prepared as 50% methane and 50% air loaded into a gas-tight 50 ml syringe. The syringes were loaded into Harvard Apparatus syringe pumps and the gas and liquid were delivered at 0.5 and 0.75 ml per hour, respectively. The gas outlet tubing was kept under 2 cm water pressure during the reaction. Fractions of liquid were collected into GC/MS autosampler vials that were kept on ice to reduce methanol evaporation and were analyzed against MeOH standards using GC/MS as described above. Methanol contamination was present in the NADH/buffer solutions, and this concentration was subtracted from the total detected in each fraction by GC/MS. No methanol contamination was found in the water used to store the PDMS. The data shown in FIG. 12B represent cumulative methanol (where the quantity of methanol produced in each fraction was added to the previous samples). Each experiment was done in triplicate; the error bars represent a standard deviation.

f. 3D Printing of PEG-pMMO Hydrogels

The printing resin was prepared with 20 vol % PEGDA 575, 10 mg/ml LAP initiator, and 2.3-5 mg/ml crude pMMO in buffer. Using projection microstereolithography (PµSL), hydrogel blocks were printed in a cubic lattice with 100 um open channels spaced 100 um apart and size dimensions from 1-3 mm. Solid and hollow cylinders of the same resin formulation were printed using the large area PµSL (LA PµSL) system. The cylinders had an inner diameter of 1-2.5 mm, an outer diameter of 3-5 mm, and were 1.5-3 mm high. The resin was cured with a 395 nm diode with both PµSL and LA PµSL but the intensity and exposure time varied between the systems, ranging from 11.3-20 W/cm$^2$ and 15-30 seconds per layer, respectively. Resin and printed hydrogels were stored on ice before and after the printing process. The pMMO activity assay was carried out as described above at 45° C. for 4 minutes. The methanol concentration of the activity assay and protein content of the printed hydrogels were measured as described above.

Applications/Uses

Embodiments of the present invention may be used in a wide variety of applications, and potentially any industrial application requiring more efficient and higher-throughput use of enzymes to catalyze chemical reactions. Illustrative applications in which embodiments of the present invention may be used include, but are not limited to, fuel conversion (e.g., natural gas to liquid fuel), chemical production, pharmaceutical production, and other processes where a chemical conversion is catalyzed by enzymes, especially at phase boundaries (e.g., reaction involving a gas and a liquid, polar and non-polar species, aqueous and non-aqueous species, etc.).

It should be noted that methodology presented herein for at least some of the various embodiments may be implemented, in whole or in part, in computer hardware, software, by hand, using specialty equipment, etc. and combinations thereof.

Moreover, any of the structures and/or steps may be implemented using known materials and/or techniques, as would become apparent to one skilled in the art upon reading the present specification.

The inventive concepts disclosed herein have been presented by way of example to illustrate the myriad features thereof in a plurality of illustrative scenarios, embodiments, and/or implementations. It should be appreciated that the concepts generally disclosed are to be considered as modular, and may be implemented in any combination, permutation, or synthesis thereof. In addition, any modification, alteration, or equivalent of the presently disclosed features, functions, and concepts that would be appreciated by a person having ordinary skill in the art upon reading the instant descriptions should also be considered within the scope of this disclosure.

While various embodiments have been described above, it should be understood that they have been presented by way of example only, and not limitation. Thus, the breadth and scope of an embodiment of the present invention should not be limited by any of the above-described exemplary embodiments, but should be defined only in accordance with the following claims and their equivalents.

What is claimed is:

1. A membrane, comprising:
a polymeric network configured to separate a first fluid and a second fluid, wherein the first and second fluids are different, wherein the polymeric network comprises a block copolymer network comprising at least two different polymers; and
a plurality of enzymatic reactive components embedded within the polymeric network, wherein at least some of the enzymatic reactive components are embedded within the polymeric network via a lipopolymer;
wherein the membrane is characterized by a multi-layer structure comprising:
a reactant-permeable layer permeable to one or more reactants of a catalytic reaction the enzymatic reactive components are configured to facilitate, and impermeable to one or more products of the catalytic reaction;
a product-permeable layer permeable to the one or more products of the catalytic reaction and impermeable to the one or more reactants of the catalytic reaction; and
an intermediate layer comprising the polymeric network, the intermediate layer positioned between the product-permeable layer and the reactant-permeable layer.

2. The membrane as recited in claim 1, wherein the plurality of enzymatic reactive components comprises one or more liposomes coupled to an enzyme.

3. The membrane as recited in claim 1, wherein the reactant-permeable layer comprises at least one polymer selected from the group consisting of:
poly(ethylene imine), poly(ether ketone), cellulose acetate, and polypropylene; and
wherein the product-permeable layer comprises at least one polymer selected from the group consisting of: poly(ethylene imine), poly(ether ketone), cellulose acetate, and polypropylene.

4. The membrane as recited in claim 1, wherein the reactant-permeable layer has a thickness in a range from about 0.1 micrometers to about 50 micrometers;
wherein the product-permeable layer has a thickness in a range from about 0.1 micrometers to about 50 micrometers;
wherein the intermediate layer is characterized by a thickness in a range from about 1 micrometer to about 2 millimeters; and
wherein the membrane has a total thickness in a range from about 10 micrometers to about 3.1 millimeters.

5. The membrane as recited in claim 1, wherein the plurality of enzymatic reactive components comprise from about 35% to about 70% of a mass of the polymer network.

6. The membrane as recited in claim 1, wherein the first and second fluids are respectively a gas and a liquid.

7. The membrane as recited in claim 1, wherein the polymeric network comprises at least one hydrophobic polymer material and at least one hydrophilic polymer material.

8. A membrane, comprising:
a polymeric network configured to separate a first fluid and a second fluid, wherein the first and second fluids are different, and wherein the polymeric network comprises a plurality of hollow tubes each characterized by a surface area to volume ratio in a range from about 1.47:1 to about 2.33:1; and
a plurality of enzymatic reactive components embedded within the polymeric network;
wherein the membrane is characterized by a multi-layer structure comprising:
a reactant-permeable layer permeable to one or more reactants of a catalytic reaction the enzymatic reactive components are configured to facilitate, and impermeable to one or more products of the catalytic reaction;
a product-permeable layer permeable to the one or more products of the catalytic reaction and impermeable to the one or more reactants of the catalytic reaction; and
an intermediate layer comprising the polymeric network, the intermediate layer positioned between the product-permeable layer and the reactant-permeable layer.

9. A membrane, comprising:
a polymeric network configured to separate a first fluid and a second fluid, wherein the first and second fluids are different; and
a plurality of enzymatic reactive components embedded within the polymeric network;
wherein the membrane is selected from the group consisting of: a microcapsule membrane, and a spiral wound membrane; and
wherein the membrane is characterized by a multi-layer structure comprising:
a reactant-permeable layer permeable to one or more reactants of a catalytic reaction the enzymatic reactive components are configured to facilitate, and impermeable to one or more products of the catalytic reaction;
a product-permeable layer permeable to the one or more products of the catalytic reaction and impermeable to the one or more reactants of the catalytic reaction; and
an intermediate layer comprising the polymeric network, the intermediate layer positioned between the product-permeable layer and the reactant-permeable layer.

10. A bioreactor, comprising:
a lattice of three dimensional structures, each three-dimensional structure comprising a membrane as recited in claim 1.

11. The bioreactor as recited in claim 10, wherein each three dimensional structure is a hollow tube having a diameter in a range from about 100 micrometers to about 10 millimeters;
wherein the lattice is characterized by a porosity of 50%; and
wherein walls of the hollow tube comprise the membrane.

12. The bioreactor as recited in claim 10, wherein the lattice is characterized by a surface area to volume ratio in a range from 1.47:1 to 2.33:1.

13. The bioreactor as recited in claim 10, wherein the first and second fluids are respectively a gas and a liquid.

14. The bioreactor of claim 10, wherein the lattice comprises a plurality of layers;
wherein at least one of the plurality of layers of the lattice is characterized by a non-uniform spacing between a plurality of three dimensional structures thereof; and
wherein a spacing between three dimensional structures of at least one of the plurality of layers is different than a spacing between the three dimensional structures of at least one other of the plurality of layers.

15. The bioreactor of claim 10, wherein the lattice comprises a plurality of layers:
   wherein at least one of the plurality of layers of the lattice is characterized by a uniform spacing between the three dimensional structures thereof; and
   wherein a spacing between the three dimensional structures of at least one of the plurality of layers is different than a spacing between the three dimensional structures of at least one other of the plurality of layers.

16. The bioreactor of claim 10, wherein the lattice further comprises a plurality of polydimethyl siloxane (PDMS) struts arranged in a three-dimensional matrix characterized by a strut spacing of 250 micrometers.

17. The bioreactor of claim 10, wherein the lattice is a cubic lattice;
   wherein the three dimensional structures define open channels of the cubic lattice; and
   wherein the cubic lattice is characterized by a spacing of 100 micrometers between the three dimensional structures thereof.

18. A method for forming the bioreactor as recited in claim 10, the method comprising: forming the lattice of three dimensional structures via microstereolithography.

* * * * *